United States Patent
Pai et al.

(10) Patent No.: US 7,053,061 B2
(45) Date of Patent: May 30, 2006

(54) AMPHOTERCIN B STRUCTURED EMULSION

(75) Inventors: Srikanth Annappa Pai, Maharashtra (IN); Sangeeta Hanurmesh Rivankar, Maharashtra (IN); Shilpa Sudhakar Kocharekar, Maharashtra (IN)

(73) Assignee: Bharat Serums and Vaccines Limited, Maharashtra (IN)

( * ) Notice: Subject to any disclaimer, the term of this patent is extended or adjusted under 35 U.S.C. 154(b) by 0 days.

(21) Appl. No.: 10/312,298

(22) PCT Filed: Jun. 19, 2001

(86) PCT No.: PCT/IN01/00119

§ 371 (c)(1),
(2), (4) Date: May 30, 2003

(87) PCT Pub. No.: WO01/97778

PCT Pub. Date: Dec. 27, 2001

(65) Prior Publication Data

US 2003/0206929 A1   Nov. 6, 2003

(30) Foreign Application Priority Data

Jun. 22, 2000 (IN) .................. 223/MUN/2000

(51) Int. Cl.
*A61K 31/70* (2006.01)
(52) U.S. Cl. ......................................................... 514/31
(58) Field of Classification Search ................... 514/31
See application file for complete search history.

(56) References Cited

U.S. PATENT DOCUMENTS 5,364,632 A * 11/1994 Benita et al. ................ 424/450
5,534,502 A * 7/1996 Seki et al. ..................... 514/31

* cited by examiner

*Primary Examiner*—Elli Peselev
(74) *Attorney, Agent, or Firm*—Thorpe North & Western

(57) ABSTRACT

Parenteral compositions of oil-coated-Amphotericin B in structured-emulsion form, having LD50 of at least 400 mg/kg in mice and process for making the same have been described. The process essentially requires dispersing Amphotericin B in oily vehicle and dispersing emulsifier in the aqueous phase. The process of present invention is simple, cost effective and gives a stable product suitable for parenteral administration. Amphotericin B emulsion compositions prepared by the process of the present invention may be administered to human beings and animals for the treatment of fungal infections, with substantially equivalent or greater efficacy and low drug toxicity as compared to the conventional composition containing Amphotericin B and sodium desoxycholate.

14 Claims, 7 Drawing Sheets

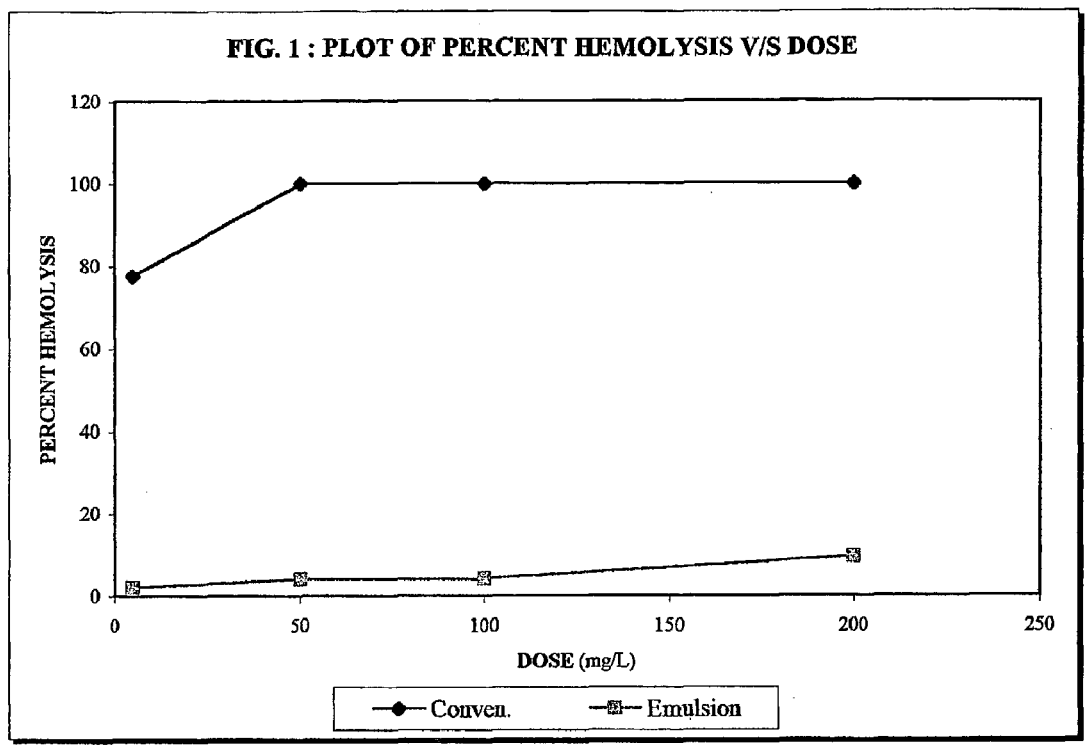
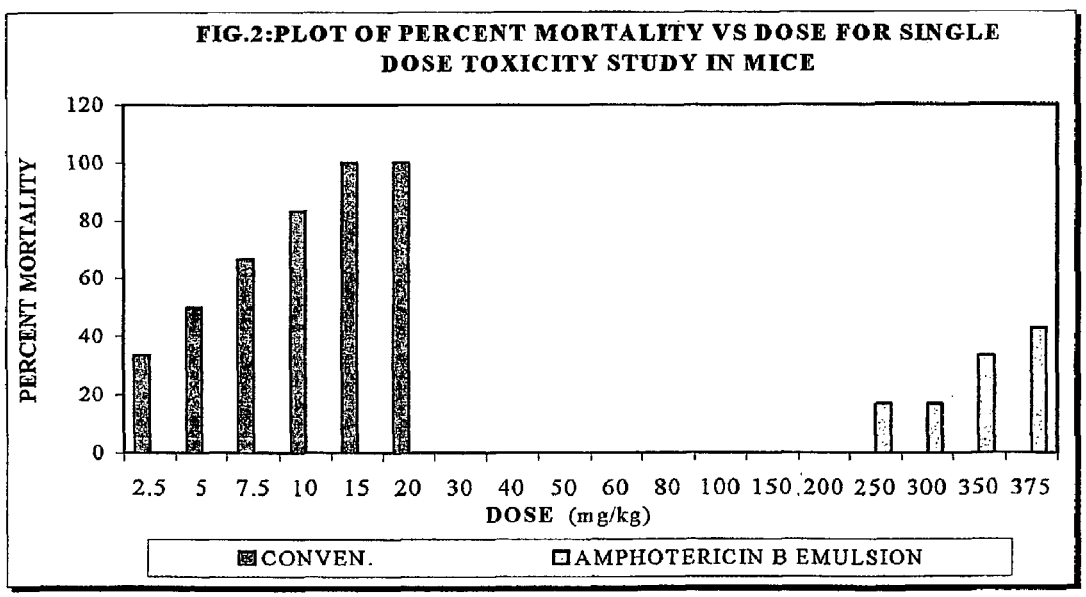

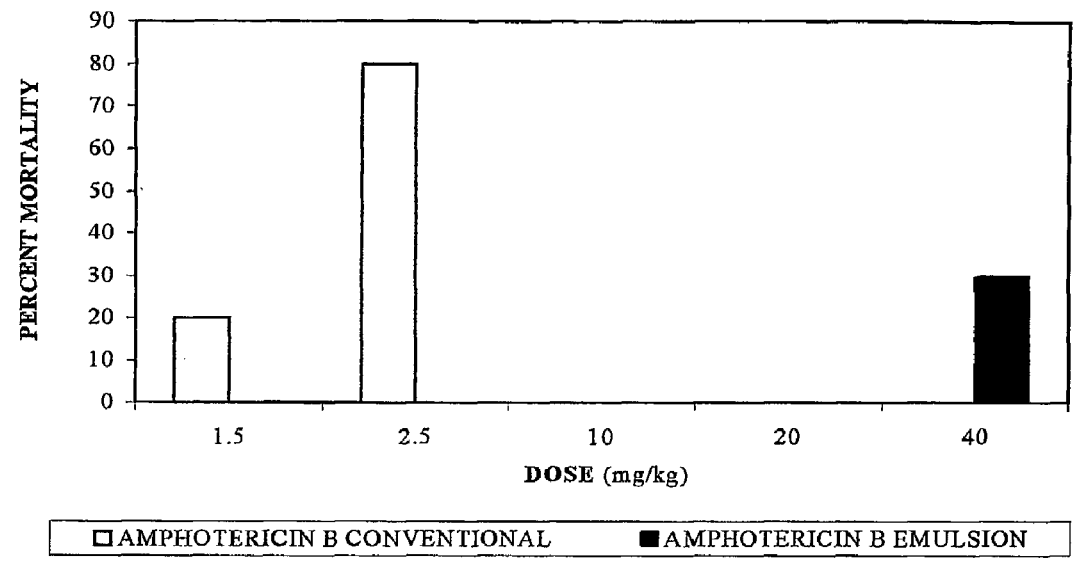
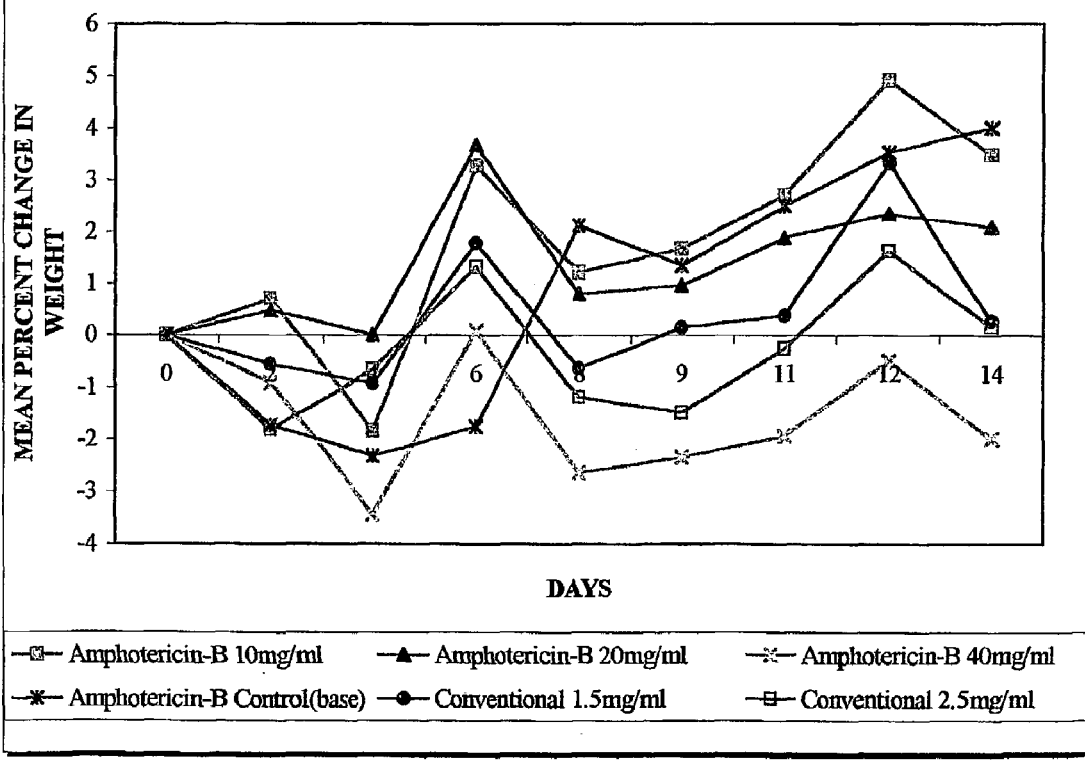

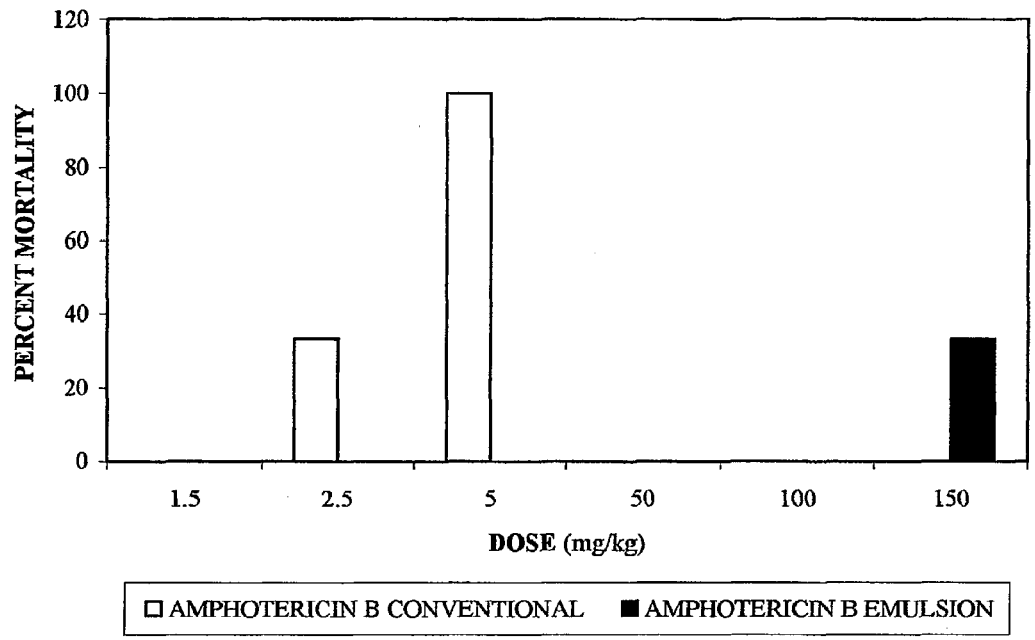
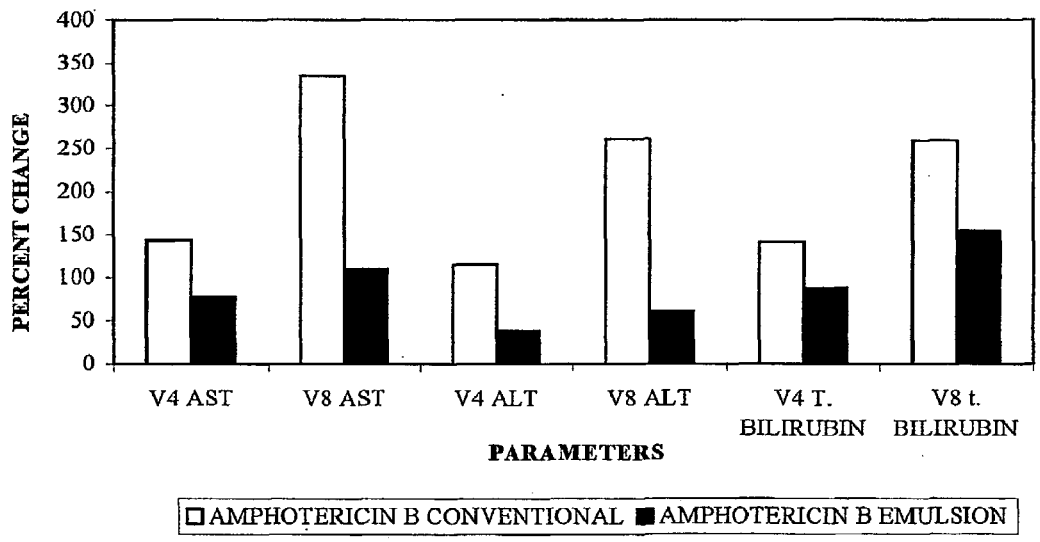

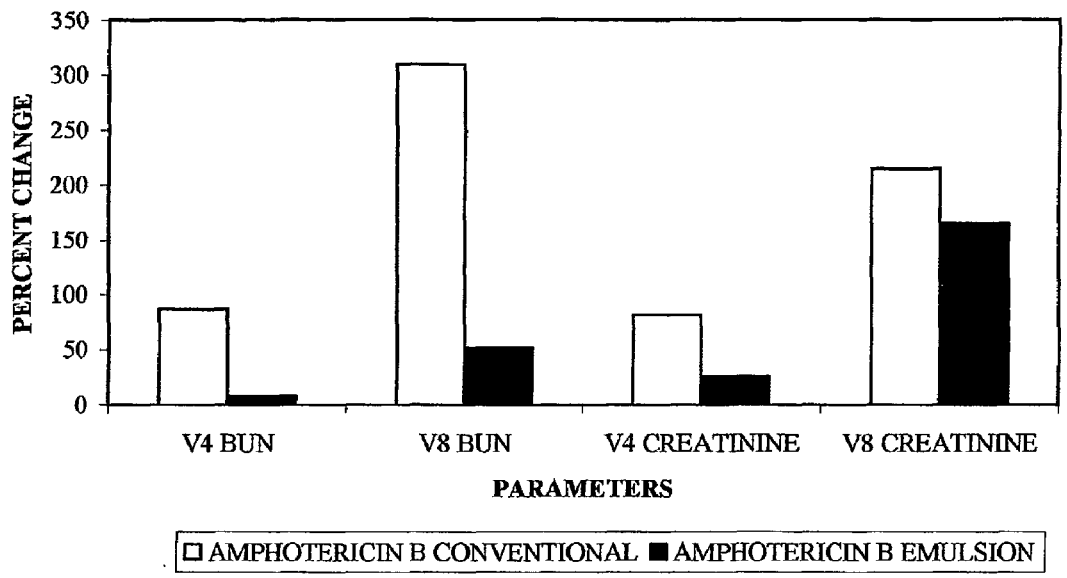
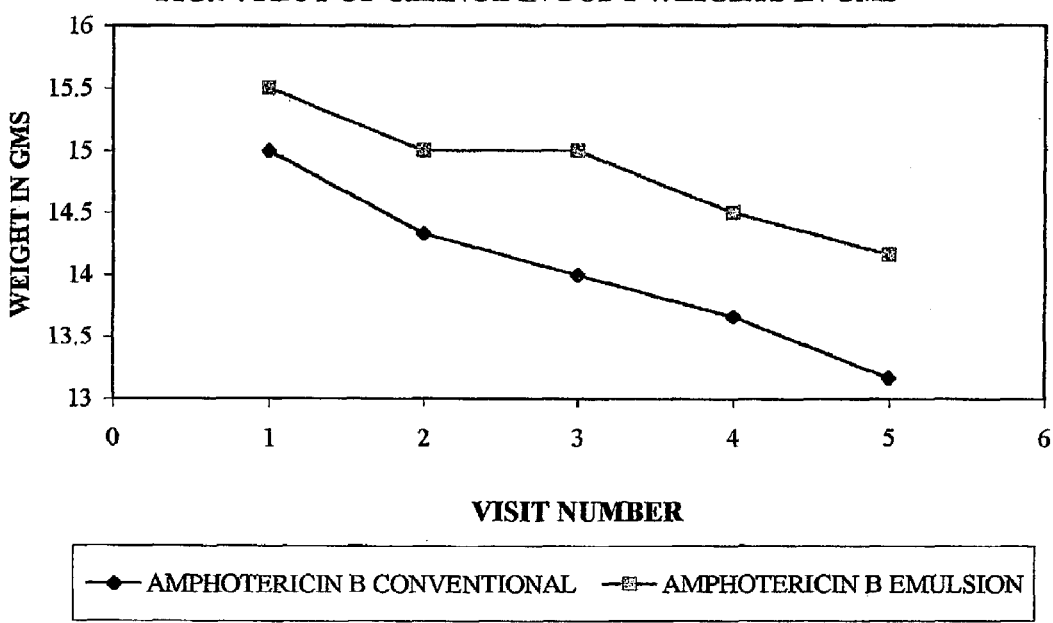

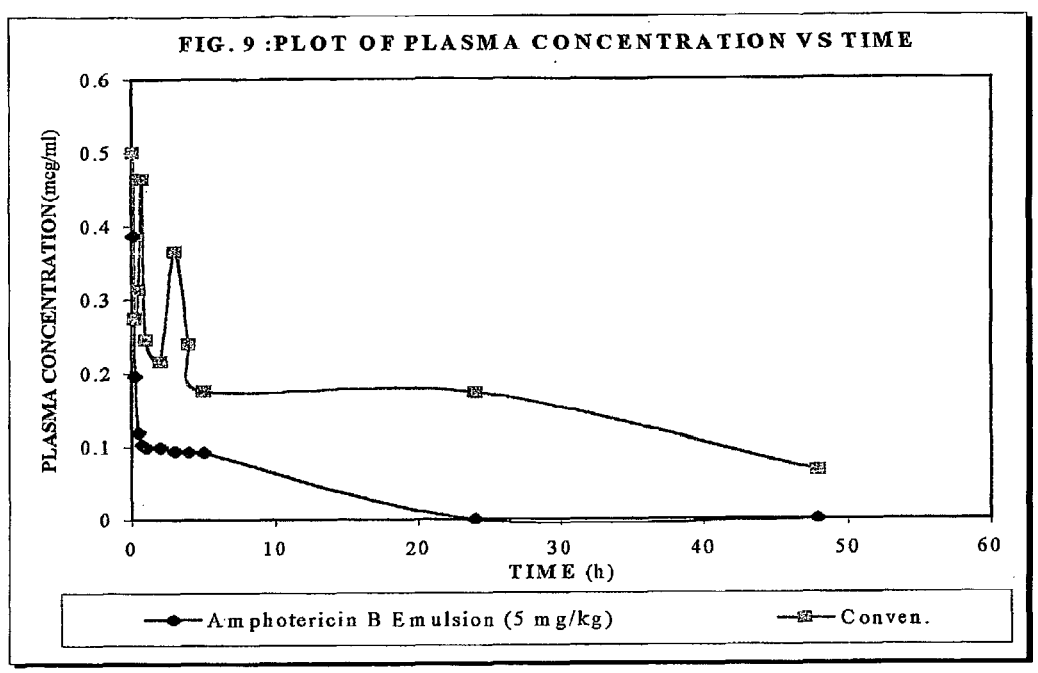

FIG. 10 : PLOT OF AMPHOTERICIN B CONCENTRATION IN DIFFERENT ORGANS FOR SINGLE DOSE STUDY IN MICE
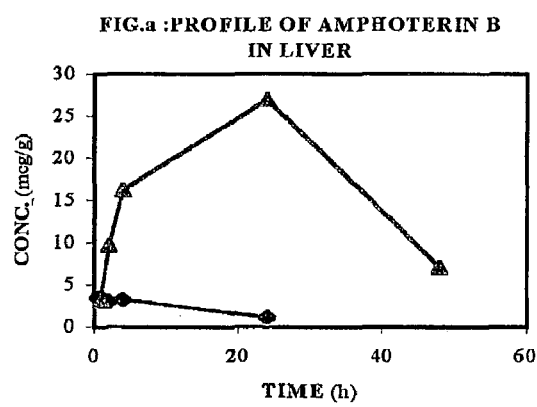
FIG.a :PROFILE OF AMPHOTERIN B IN LIVER
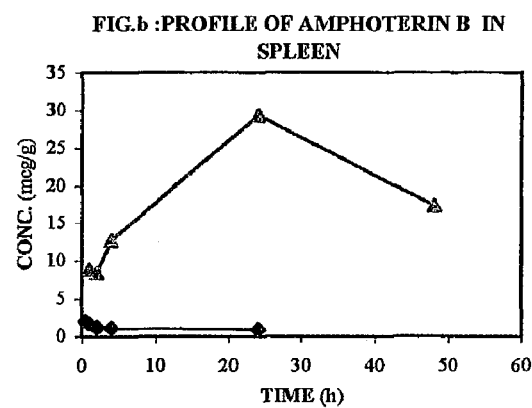
FIG.b :PROFILE OF AMPHOTERIN B IN SPLEEN
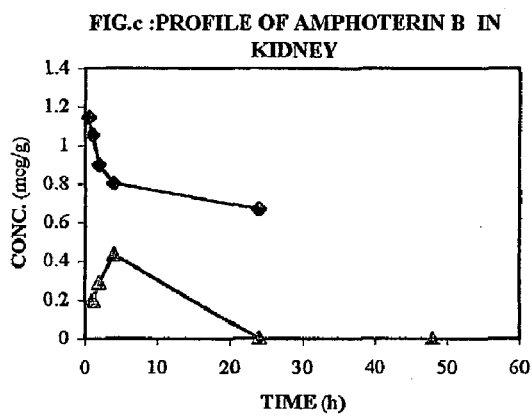
FIG.c :PROFILE OF AMPHOTERIN B IN KIDNEY
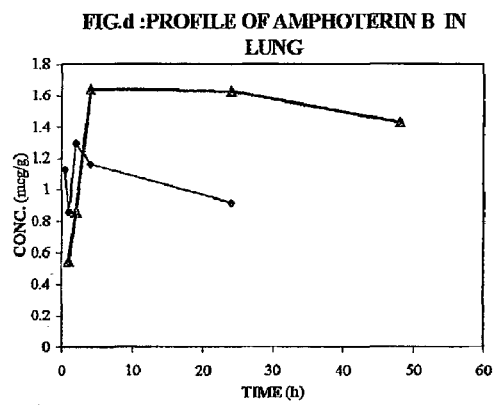
FIG.d :PROFILE OF AMPHOTERIN B IN LUNG
◆ Conventional Amphotericin B Injection      ▲ Emulsion FIG. 11 : PLOT OF AMPHOTERICIN B CONCENTRATION IN DIFFERENT ORGANS OR REPEAT DOSE STUDY IN MICE
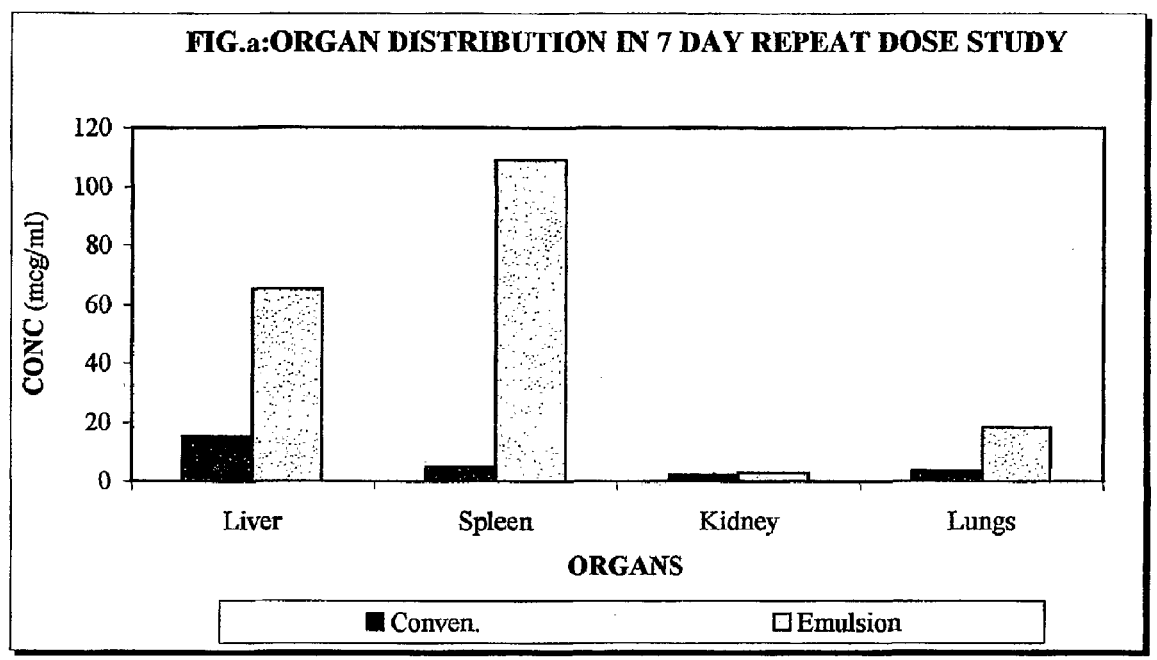
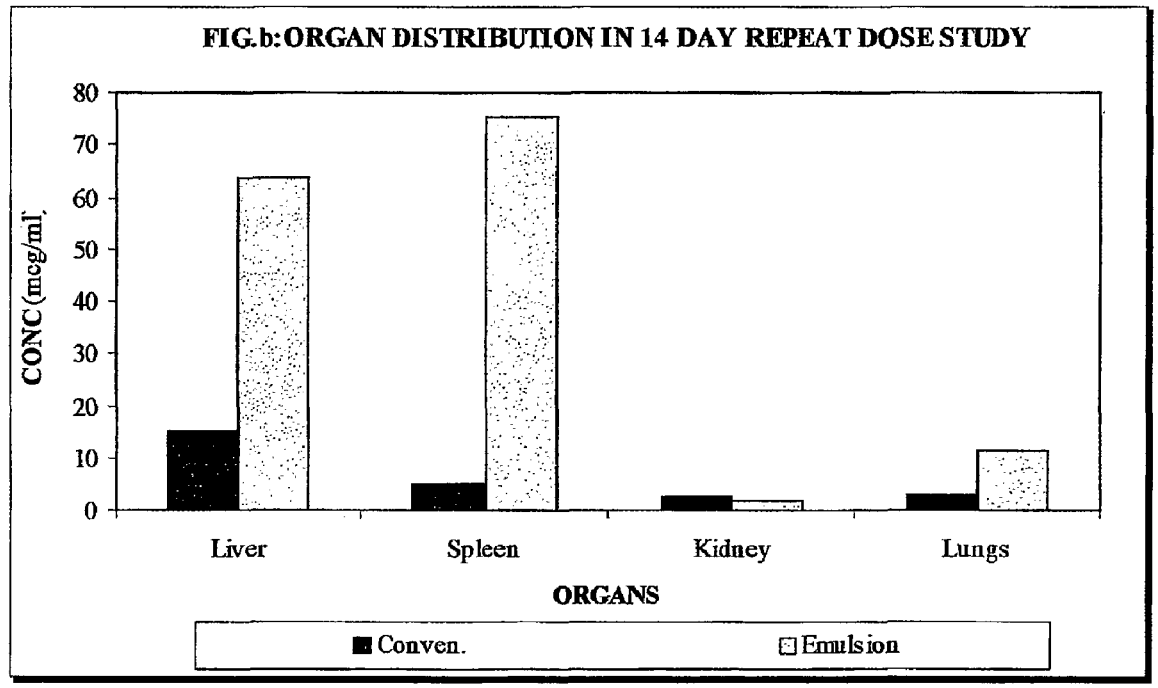

# AMPHOTERCIN B STRUCTURED EMULSION

FIELD OF INVENTION

This invention relates to Amphotericin B composition with low toxicity. This invention particularly relates to Amphotericin B composition with low toxicity in a structured emulsion of oil-in-water type for parenteral administration.

BACKGROUND OF THE INVENTION

Amphotericin B is a macrocyclic, polyene antibiotic produced by Streptomycetes nodosus. It is effective against a broad variety of fungi, yeasts and some protozoans.

Amphotericin B for intravenous administration was originally available in a conventional colloidal form. Even today, about 35 years after its development, it is widely used as an important antifungal agent because of its reliable therapeutic efficacy. The tolerability of the drug is low in view of number of adverse effects reported when used clinically. Nephrotoxicity occurs in almost all patients receiving conventional Amphotericin B intravenously. The other adverse effects include hypertension, hypotension, cardiac arrhythmia including ventricular fibrillation, cardiac arrest, liver disorders. Both tubular and glomerular damage occurs and there is a risk of permanent impairment of renal function. Solutions of Amphotericin B irritate the venous endothelium and may cause pain and thrombophlebitis at the injection site because of the synthetic surfactant sodium deoxycholate used in the preparation to solubilise Amphotericin B.

To reduce the toxic effects, Amphotericin B has been formulated in different drug delivery systems such as lipid complex, liposomes and emulsion. These compositions have greater efficacy, yet have a lower toxicity in comparison with the drug when used in the free form. Both the lipid complex and liposomal formulations of Amphotericin B are now available in the market and are approved in various countries worldwide.

The main disadvantage of lipid formulations based on lipid complex and liposome, is the high cost of therapy. Amphotericin B is a lipophilic drug that binds to sterols and intercalates into lipid bilayers and hence Amphotericin B is particularly suitable for use with the lipid-based delivery systems.

An attempt in this laboratory was made to formulate Amphotericin B in the form of a lipid based emulsion which have the benefits of low toxicity at lower cost of therapy.

Volker Heinemann et. al. have postulated [Antimicrobial agents and chemotherapy 1997, 41(4); 728–732] that the lipid emulsions decrease the amount of oligomeric Amphotericin B and thereby reduce the interaction of Amphotericin B with cholesterol of human cell membranes. The remaining monomeric Amphotericin B however retains its potential to bind to the ergosterol of fangal cell membranes.

Kirsh R. Goldstein R, Tarloff J, and et. al have reported (J. Infect. Dis. 1988, 158; 1065–1070) that the lipid emulsion composition of Amphotericin B prepared by mixing with fat emulsion have low toxicity without loss of antifungal activity. However, the physical stability of such lipid emulsion carrying Amphotericin B has been found to be poor.

Moreau P, et. al have reported (J. Antimicro. Chemother. 1992, 30; 535–541) that patients treated with fat emulsion mixed with Amphotericin B injection appeared to have a significant reduction in infusion related toxicity and renal dysfunction.

The use of Amphotericin B mixed with fat emulsion of parenteral nutrition are increasing both in Europe and United States.

The prior art processes of making Amphotericin B emulsion are discussed below:

U.S. Pat. No. 5,364,632 (1994)/Japanese Patent JP 2290809 (1990)

The process or preparation of an emulsion in accordance with this invention is described in a typical example as follows:

Amphotericin B was dissolved in methanol (0.8 mg/ml) by bath sonication (15 minutes). Phospholipids E-80 (containing mainly 80% phosphatidyl choline and 8% phosphatidyl ehanolamine) were dissolved in chloroform. Both solutions were mixed and filtered through a combined filtering system comprising a fibre glass prefilter and 0.45µ regenerated cellulose membrane filter (RC 5) (GF92) for removing pyrogens and aggregates. The resulting clear lipid solution was deposited as thin film on the walls of a round bottom flask by rotary evaporation under reduced pressure at 40° C. The aqueous phase comprising the poloxamer, sodium deoxycholate and glycerin was filtered through a 0.22 µ Millipore filter, poured into the flask and the dispersion was sonicated until a homogenous liposomal mixture was achieved.

MCT (Medium chain triglyceride) oil, filtered through 0.22 µ Millipore filter, and containing α-tocopherol was heated to 70° C. and then admixed into the liposomal mixture heated to 45° C. and dispersed therein by a magnetic stirrer.

Emulsification was carried out while maintaining the same temperature using a high shear mixer, Polytron. The resulting coarse emulsion was cooled rapidly. A fine monodispersed emulsion was achieved using a two-stage homogeniser.

Finally, the pH of the emulsion was adjusted and was filtered through a 0.45 µ Mllipore filter to discard coarse droplets and debris generated during the emulsification and homogenisation process.

All processing operations were carried out under aseptic conditions.

The relative amounts of the various ingredients in the final emulsions in the Example and the range given in the description are as follows:

Amphotericin B 0.075% (0.015–0.15%), MCT oil 20% (3–50%), phospholipid E80 0.5% (0.5–20%), poloxamer 2% (0.3–10%), sodium deoxycholate 1% (0.5–5%), glycerin 2.25%, α-tocopherol 0.02% and double distilled water 200%.

The drawbacks of U.S. Pat. No. 5,364,632 (1994)/Japanese Patent JP 2290809 (1990) process are:

i. As the solubility of Amphotericin B in methanol is low, a large amount of methanol is required to dissolve the required quantity of Amphotericin B. This restricts the level of the drug in the final composition.

ii. In this process it is necessary to first form a thin film of the drug, Amphotericin B and phospholipids, and then to hydrate that film using the aqueous phase. The aqueous phase contains non-ionic emulsifying agent poloxamer, surfactant sodium deoxycholate and glycerin.

iii. The oil phase used is MCT oil with added α-tocopherol. The emulsion is prepared by adding the oily phase maintained at 70° C. to aqueous phase maintained at 45° C. This does not ensure that the Amphotericin B is retained in the oil phase. This process does not exploit the full potential of reducing the toxicity of the Amphotericin B if it were to be placed in the oily phase.

iv. The product of the process of U.S. Pat. No. 5,364,632 (1994) is made under aseptic conditions to render it sterile. The preferred process of sterilisation specified in pharmacopoeias is autoclaving of the product in the final container. Further as Amphotericin B is commonly administered by intravenous route, terminal sterilisation is the only preferred alternative which offers higher confidence of sterility compliance.

v. The emulsion product eventhough is stable to mechanical stress, has not been studied for toxicity. The toxicity of the product hence is not known. However in-vivo comparative studies have been done in Balb/c mice in comparison with Fungizone, which is a commercial Amphotericin B formulation containing Sodium deoxycholate. This study indicated that the product is less toxic than Fungizone.

vi. The use of MCT oil and the poloxamer increases the plasma concentration of the drug by reducing the uptake of the drug by reticulo endothelial system (RES). In case of fungal infections, Amphotericin B is required to be distributed in the reticulo-endothelial system, which is the site of infection.

Japanese Patent 11-60491 (1989)

In this Japanese Patent a medicinal formulation containing Amphotericin B in the emulsion form has been described. The emulsion contains i) Amphotericin B (1 to 10 mg/ml of final emulsion).

ii) the oily phase—The oily phase consists of plant oils, fish oil or triglycerides, (1–50%, preferably 5–30%). The preferred oil used is soybean oil or sesame oil.

iii) emulsifiers—The emulsifier used are phospholipids. Additionally non-toxic emulsifiers are also employed. Phospholipids used are such as egg yolk phospholipids, soybean phospholipids, or hydrogenated product obtained from these materials. Phosphatidylcholine, Phosphatidyl ethanolamine, phosphatidyl inositol, phosphatidyl serine, phosphatidic acid, phosphatidyl glycerol have also be used. The quantity recommended is 1–50% by weight of the oil component, preferably 10–30% by weight of the oil component or 1–10% w/v, preferably 4–6% w/v of the emulsion.

Non-ionic emulsifiers such as polyalkylene glycol (mol. wt. 1000–10000, preferably 4000–6000); or polyoxyethylene or polyoxy propylene polymer) (mol. wt. 1000–20000, preferably 2000–10000), hydrogenated castor oil polyoxy alkylene derivatives such as hydrogenated castor oil polyoxyethylene-20-ether, -40-ether, -100-ether less than 5% w/v preferably less than 1% w/v are employed. A combination of the two non-ionic emulsifiers can also be used.

iv) fatty acids and their salts (Pharmaceutically acceptable)—upto 1% preferably 0.5% w/v.

v) stabilisation agents less than 5% w/v, preferably less than 1% w/v which include
  a) high molecular weight polymer substances such as albumin of human origin; vinyl copolymer e.g. polyvinyl pyrolidone, polyvinyl alcohol; aliphatic amines.
  b) gelatin, hydroxy ethyl starch; Cholesterol varieties, vi) isotonic agents—less than 5% w/v preferably less than 1% w/v.

vii) glycerin or its monoesters like mono olein, mono palmitin;

viii) saccharides such as mono and disaccharides, sorbitol, xylitol less than 5% w/v preferably less than 1% w/v.

ix) antioxidants such as tocopherol less than 5% w/v preferably less than 1% w/v;

x) pH controlling agents such as acids, alkalies and buffers.

The process of manufacturing followed is said as reported in the past. This process involves first forming water-in-oil emulsion (w/o) and then converting it into oil-in-water emulsion (o/w) by dilution with water. In this process, soybean oil, phospholipid, Amphotericin B and some water as well as other additives (whenever used) are all mixed together and heated if required. The mixture is then homogenised in high-pressure homogeniser. More water is added in the required quantity to convert w/o emulsion into an o/w emulsion, which is homogenised again.

In a typical example, 200 g of soybean oil, 50 g phospholipid and 2.5 g Amphotericin B and 750 ml water are processed as above.

In another example glycerin 2.2% w/v of the composition has been incorporated in the above composition.

The mean emulsion droplet size is from 0.1–0.2μ. The emulsion and its droplet size is stable up to 10 days under refrigeration conditions.

Drawbacks of this Japanese Patent 11-60491 (1989) process are:

It is known that Amphotericin B in emulsion formulation is less toxic than the conventional Amphotericin B formulation. However, the formulations of this Japanese Patent 11-60491 (1989) does not exploit the full potential of reducing toxicity available to this emulsion concept, because of the process of making the emulsion followed in this patent.

i. Because of the mean particle size of the emulsion obtained in the Japanese patent JP 11-60491 (1989) is from 0.1 to 0.2μ, it is unable to exploit the well-known benefit of the preferential uptake of particles larger in size by reticuloendothelial system. Preferential uptake of Amphotericin B by reticuloendothelial system is required, as this is the site for most of the fungal infections.

ii. The stability of the emulsion is studied up to 10 days in refrigerator.

iii. A large number of additives which include emulsification supporting agents such as aliphatic amines, high molecular wt. polymers, nonionic nature surface active agents, cholesterol varieties, saccharides such as mono and disaccharides, antioxidants are suggested for addition in the emulsion formulation.

iv. The process step of making the product sterile has not been specified.

In Japanese Patent 4-173736 (1992), a product containing 0.005% to 5% Amphotericin B, 0.5% to 25% phospholipid, preferably egg lecithin has been described. The composition has an average particle size diameter of 100 nm. This is not an emulsion and does not contain any oil phase.

In U.S. Pat. No. 5,389,373 (1995), a process of preparing an oil in water (o/w) emulsion of poorly soluble drugs is described. The process involves dissolving Amphotericin B in aqueous solution of high or low pH, adding the resulting solution of not more than 100 μg/ml strength to a preformed emulsion, adding to the emulsion an amount of acid, base or buffer appropriate to neutralise and to adjust the pH of the product to a desired value.

Drawbacks of this U.S. Pat. No. 5,389,373 (1995) process are:

The main weakness of this process is the limitation of the low strength of the Amphotericin B into the emulsion. In this process, Amphotericin B concentration is of the order of 100

μg/ml. Hence a larger volume of the composition is required to be injected which is therapeutically not advantageous.

In U.S. Pat. No. 5,534,502 (1996), Amphotericin B is decrystallized using an acid and ethanol and then homogeneously dispersed in a lipid, following which it is emulsified. In this process it is essential to dissolve Amphotericin B in ethanol, the most preferred quantity of ethanol is 400 to 600 ml/gm of Amphotericin B. The main weakness of this process is Amphotericin B is not stable in acid pH.

European Patent EP 0700678 (1996) describes a lipid emulsion which essentially contains citric acid or a pharmaceutically acceptable salt thereof and at least one member selected from the group consisting of methionine, phenylalanine, serine, histidine and pharmaceutically acceptable salts thereof, provided that it does not simultaneously contain methionine and phenylalanine.

It is an essential requirement to simultaneously use citric acid and at least one of the above amino acids. The process of preparation of an emulsion in accordance with this invention is described as follows:

Phospholipids and auxiliary agents for emulsification such as oleic acid are dissolved in an appropriate organic solvent such as hexane and then the solvent is distilled off under reduced pressure to give a lipid film. To the resulting lipid film, oil component and water and the mixture is preliminarily emulsified by vigorously stirring through shaking. The resulting liquid is emulsified using the currently used emulsifier. After completion of the emulsification the pH value of the resulting emulsion is adjusted to a predetermined level by addition of Hydrochloric acid or Sodium hydroxide. Then citric acid and amino acid are added to the emulsion to give a lipid emulsion. Alternatively the lipid emulsion likewise be prepared by adding an oil component and an aqueous solution of citric acid and amino acids to the lipid film prepared by the foregoing procedures and then subjecting the resulting mixture to the emulsification procedures.

Drawbacks of this European Patent EP 0700678 (1996) process are:

The process of making Amphotericin B emulsion has not been described specifically. Amphotericin B is one of the drugs from a list of about 70 drugs that is stated as "may be formulated in lipid emulsion".

i) The process of preparing lipid emulsions involve dissolving phospholipids in appropriate organic solvents such as hexane.

ii) In the examples of this patent, amino acids and citric acid are added to the preformed lipid emulsions and the stability studied at 60° C. for discolouration. Intravenous emulsions are required to be stable to sterilisation temperatures of autoclaving.

iii) The process of sterilisation specified in one of the examples is heating at 60° C. for 1 hour and repetition of this sterilisation process three times every 24 hours. This process is not suitable for preparing intravenous injections.

The main object of the present invention is to develop a process for Amphotericin B emulsion useful for parenteral administration, having very low toxicity and to overcome the drawbacks and weaknesses of the prior art processes enumerated above.

Thus the principal part of the main object is to develop a process for coating solid powder of Amphotericin B with oil and placing the oil coated solid Amphotericin B powder in the oily phase of the oil-in-water emulsion with the provision for retaining the Amphotericin B incorporated in the oily phase of the emulsion throughout the entire process of manufacturing including autoclaving process of sterilisation and thereafter till its shelf life or use.

Another part of the main object is to develop a process for making such structured oil-in-water emulsion with average oil droplet in the emulsion controlled in the optimum range so that it is preferentially distributed in reticulo-endothelial system giving a low plasma concentration. Thus for injectable purpose it acts like aqueous outer phase emulsion carrying oil globules containing oil coated Amphotericin B.

Another part of the main object is to develop a process for making such structured Amphotericin B emulsion that will need only minimum of additives, which are essential for making an oil-in-water emulsion.

SUMMARY OF THE INVENTION

Accordingly, the present invention relates to a parenteral composition of oil-coated-Amphotericin B in structured-emulsion form, having $LD_{50}$ of at least 400 mg/kg in mice, comprising a) oily phase (upto 30% w/v of the composition) selected from group of vegetable oils such as soybean oil, sesame oil, safflower oil;

b) Amphotericin B (0.05% to 1% w/v of the composition) dispersed in oily phase;

c) aqueous phase water;

d) tonicity modifying agents selected from a group of compounds such as glycerin, mannitol, dextrose dissolved in aqueous phase and;

e) emulsifier such as natural phosphatides (up to 3% w/v of the composition) dispersed in aqueous phase.

In another embodiment, this invention is related to the process for manufacture of a parenteral composition of oil-coated-Amphotericin B in structured-emulsion form, having $LD_{50}$ of at least 400 mg/kg in mice, comprising dispersing Amphotericin B in oily phase; preparing aqueous phase by dissolving tonicity modifying agent in water; dispersing the emulsifying agent in the aqueous phase; adjusting pH of the aqueous phase to about 8–11; adding the oily phase to the aqueous phase under stirring to obtain a coarse structured-emulsion; homogenising the coarse structured-emulsion to a particle size below 2 microns; filtering, filling the homogenised structured-emulsion into glass containers under nitrogen, closing the glass containers, sealing the closed glass containers and sterilising the sealed filled containers by autoclaving. The order of these process-steps is important. Altering the order of these process-steps changes the structure of the emulsion as reflected by toxicity studies.

It is characteristic of the process of the present invention that the egg phosphatide is dispersed in aqueous phase while the Amphotericin B powder is dispersed in oily phase and therefore the product is referred to as oil-coated-Amphotericin B in structured-emulsion form.

In another embodiment, this invention is related to a parenteral composition of oil-coated-Amphotericin B in structured-emulsion form as manufactured by the process described above.

Formulating Amphotericin B as structured-emulsion form of oil-in-water type by the process of the present invention, resulted in reducing its toxicity considerably and ensured sterility of the composition without altering its antifungal activity. The composition of the present invention, being less toxic, provide scope for increasing the dose levels in treating certain infections.

The parenteral composition of oil-coated-Amphotericin B in structured-emulsion form of the present invention is less toxic and is characterised by
a) having $LD_{50}$ of at least 400 mg/kg body weight in single dose toxicity study and of at least 40 mg/kg body weight in repeat dose toxicity study in mice;
b) having $LD_{50}$ of at least 150 mg/kg body weight in rats in single dose toxicity study;
c) having at least 20 times less hemolytic effect on human red blood corpuscles when compared to conventional formulation containing sodium deoxycholate;
d) having preferential tissue distribution in reticular endothelial system and having at least twice the $t_{1/2}$ in organs of reticulo-endothelial system compared to the conventional formulation containing sodium deoxycholate in single dose study in mice;
e) having no toxic symptoms of cardiac toxicity after injecting in mice such as severe respiratory distress, local irritation, abdominal distress, and agitation.

DETAILED DESCRIPTION OF EMBODIMENTS OF THE INVENTION

The Amphotericin B content in the parenteral composition of oil-coated-Amphotericin B in structured-emulsion form of the invention is broadly in the range of 0.05% to 1% w/v of the composition. Preferably it is from 0.1 to 0.5% w/v and specifically it is either at about 0.5% or at about 0.25% w/v of the composition.

In the process of the present invention Amphotericin B is dispersed in oily phase prior to emulsification. Amphotericin B is used as such or is micronised before dispersing in oily phase. Oily phase is present in an amount that is broadly up to 30% w/v of the composition, preferably from 5 to 25% w/v and more preferably it is 10–20% w/v, specifically it is either at about 10% w/v or at about 20% w/v. Typically the oily phase used is a vegetable oil and can be one of the vegetable oils such as soybean oil, sesame oil, cotton seed oil, safflower oil, sunflower oil, arachis oil, corn oil, castor oil or olive oil. Preferred vegetable oil is soybean oil.

In this invention emulsifier is dissolved in aqueous phase. Suitable emulsifiers include naturally occurring phosphatides and modified phosphatides. Preferred emulsifier is naturally occurring phosphatides such as egg phosphatide and soya phosphatides. Emulsifier used in the present invention may comprise a mixture of two or more of the above mentioned emulsifiers. The preferred natural phosphatide is purified egg phosphatide.

The parenteral composition of oil-coated-Amphotericin B in structured-emulsion form of the present invention is formulated for the pH range 6.0–8.5. In the process of present invention pH of the aqueous phase is adjusted between 8 & 11 with an alkali such as sodium hydroxide or potassium hydroxide solution in water so that the pH of the composition of the present invention after autoclaving remains in the range of 6–8.5.

The parenteral composition of oil-coated-Amphotericin B in structured-emulsion form of the present invention is made isotonic with blood by incorporation of a tonicity modifying agent such as glycerin, mannitol, dextrose, or a combination thereof. Preferred tonicity modifying agent is glycerin. Glycerin is present in an amount from 2–3% w/v of the composition. Preferably amount of glycerin used is about 2.25% w/v of the composition.

The parenteral composition of oil-coated-Amphotericin B in structured-emulsion form of the present invention are specifically sterile oil-in-water emulsions, prepared according to the manufacturing procedures under controlled conditions and are terminally sterilised by autoclaving. When the emulsification is carried out at a higher temperature, either aqueous phase or oily phase or both phases are maintained at a temperature upto 75° C.

The average particle size of the composition of the present invention is deliberately kept up to 2μ so that Amphotericin B preferentially gets distributed in the reticulo-endothelial system thereby giving low plasma concentration.

The present invention is described by a typical Example wherein the structured emulsion comprising Amphotericin B (0.5% w/v); oily phase soybean oil (20% w/v); emulsifier purified egg phosphatide (1.2% w/v); tonicity modifying agent glycerin (2.25% w/v) and; water (q.s. to 100% by volume); as manufactured by the process comprising dispersing Amphotericin B in soybean oil; preparing aqueous phase by adding glycerin to water; followed by dispersing the purified egg phosphatide in the aqueous phase; adjusting pH of the aqueous phase to 10.8; adding the soybean oil containing Amphotericin B to the aqueous phase under stirring to obtain a coarse emulsion; homogenising the coarse emulsion to a particle size below 2 microns; filtering through 2 micron filter, filling into glass containers under nitrogen, closing the glass containers, sealing the closed glass containers and sterilizing the sealed filled containers by autoclaving.

The structured emulsion of the parenteral composition of oil coated Amphotericin B structured in oil-in-water type emulsion of the present invention has low toxicity and it has low particle size and it is suitable for parenteral use. Sterility of the composition of the present invention is assured because the product is sterilised by end autoclaving without significant loss of Amphotericin B activity and without destabilising the emulsion. The composition of the present invention is easy to use as the product could be diluted with dextrose injection 5% or saline to get the required concentration for parenteral administration. The composition of the present invention also has a prolonged shelf life and hence suitable as a ready marketable product.

We have studied toxicity profile of the emulsions prepared by the processes in which variations were made in the mode of addition of Amphotericin B and purified egg phosphatide. These are described in the Examples as given in the following Table.

| Example | Amphotericin B | Egg Lecithin | Toxicity |
| --- | --- | --- | --- |
| I | In oily phase | In aqueous phase | Does not show symptoms of cardiac toxicity |
| IV | In aqueous phase | In aqueous phase | Shows symptoms of cardiac toxicity |
| V | In aqueous phase | In oily phase | Shows symptoms of cardiac toxicity |
| VI | In oily phase | In oily phase | Shows symptoms of cardiac toxicity |

In the process of present invention, when Amphotericin B, suspended in an aqueous phase is observed to give a product which on injection into mice produced symptoms of cardiac toxicity such as severe respiratory distress, local irritation, abdominal distress and agitation. However these toxic symptoms were not observed when Amphotericin B is suspended in oily phase. This could be because of reservoir effect due to both the oily droplets of the emulsion and the Kuppfer cells. This slow release could lead to the presence of monomeric Amphotericin B in plasma following injection of emulsion formulation thereby reducing the toxicity [Ref Antimicrobial agents and chemotherapy, 1997; Vol. 41(4): Pg. 728–732].

We found that the composition prepared by adding the emulsifier egg lecithin in oily phase also produced symptoms of cardiac toxicity as mentioned above. After extensive experimentation this problem was overcome by adding egg lecithin to aqueous phase. These process studies are described in Example I to Example VI. Example II and Example III which are the variations of Example I are all of the present invention, while Examples IV, V and VI are not of invention. Example VII describes the in-vitro toxicity studies against human red blood corpuscles. Example VIII and Example XI describe the toxicity studies in mice, rats and dogs. Example IX describes pharmacokinetic study in rabbits and Example X describes organ distribution studies in mice.

The observation that Amphotericin B dispersed in oil and egg lecithin dispersed in water gives an emulsion with a very low toxicity suggests a strong interaction between oil droplets and Amphotericin B. Therefore Amphotericin B emulsion may be considered as a reservoir of monomeric form of Amphotericin B, and due to the high stability of the formulation, only limited amounts of free Amphotericin would be progressively released. The monomeric form of Amphotericin B is able to bind to the ergosterol of fungal cells but is inactive against the cholesterol of host mammalian cells and hence causes less toxicity. In case of conventional Amphotericin B formulation, the release of high free Amphotericin B levels in the plasma leads to the presence of self-associated oligomers in the circulation. These oligomeric forms interact with cholesterol containing host cell membranes and hence cause more toxicity. This explains the mechanism of low toxicity of Amphotericin B emulsion of the present invention in comparison with the conventional formulation. Lower peak concentration and AUC values in serum (Example IX) and correspondingly faster deposition of Amphotericin B in tissues (Example X-A) also explains the reason for the lower toxicity of the Amphotericin B emulsion of the present invention. Low toxicity is confirmed by our findings as given in the Examples VIII-A, VIII-B and VIII-C These toxicity studies show that though the parenteral composition of oil-coated-Amphotericin B in structured-emulsion form of the product of our present invention appears similar to that of the one described in Japanese Patent 11-60491 (1989), the product of the present invention has characteristic biological low toxicity because of the process of manufacture.

The process of the present invention gives an emulsion product which favours formation of monomers because of the slow release of Amphotericin B in plasma when injected which is not happening with the product made by the process described in Japanese Patent 11-60491 (1989). Thus the emulsion structure of the present invention is different from that obtained by Japanese Patent as characterised by the toxicity studies. Therefore we call the emulsion of present invention as structured emulsion.

In main embodiment of the invention, Amphotericin B is dispersed in oily phase so that Amphotericin B powder is oil coated. Egg lecithin used as an emulsifier is dispersed in aqueous phase.

In another embodiment of the invention, the homogenisation is done in repeated cycles to achieve particle size distribution below 2 μ.

In another embodiment of the invention, the final parenteral composition of oil-coated-Amphotericin B in structured-emulsion form is terminally sterilised by end autoclaving.

Distinctions from Prior Art:

It will be seen from the following that the process of the present invention is different from the Patent.

a) The process of present invention is different from the U.S. Pat. No. 5,364,632 (1994) in not using any solvent for Amphotericin B; in not going through process of preparation of a film of Amphotericin B and phospholipid and subsequent hydration; in not using MCT oil with added α-tocopherol; in adjusting pH of the aqueous phase containing egg phosphatide to 8–11; in having a terminal sterilisation step—and in the product which has low toxicity and good distribution in reticulo-endothelial system (RES).

Use of such large quantity of solvent makes the process difficult to adopt commercially. The particle size in different examples has been found to be less than 100 nm, however the toxicity of the composition has not been reported.

In the process of present invention, the low toxicity is maintained even at 5 mg/ml which is therapeutically advantageous as the volume required to be injected is low.

b) The process of present invention is different from the Japanese Patent 11-60491 (1989) in that the emulsion globule/particle size is 0.1–0.21μ in the Japanese Patent and that in the present invention is up to 2 μ.

In the process of our invention egg phosphatide is added to the aqueous phase and the pH of aqueous phase is adjusted to 8–11.

The shelf life of the product of the present invention is over 2 years whereas that of the Japanese Patent is of the order of 10 days or a few weeks.

A large number of emulsion supporting agents are required in the process of the Japanese patents which are not required in the present drug emulsion.

The process of present invention provides a sterile product, terminally sterilised by autoclaving, that of the prior art Japanese Patent is not sterilised, c) The product made by the process of Japanese Patent 4-173736 (1992) does not contain particles having diameters of more than 1 μm and this product does not contain an oil component and hence is different from the composition of the present invention.

d) In U.S. Pat. No. 5,389,373 (1995), Amphotericin B is added to a preformed emulsion whereas in the process of our present invention, Amphotericin B dispersed in oily phase.

e) In European Patent EP 0700678 (1996), Amphotericin B emulsion as such has not been described. It is one of the drugs out of about 70 drugs specified in the patent as "may be formulated as lipid emulsion".

The emulsions described in this patent essentially should have amino acids and citric acid or its salts which are not at all required in the process of our invention.

The process of making emulsion in this patent essentially starts with making a phospholipid film with or without a drug. This procedure is not at all followed in the process of our invention.

In the process of making emulsion the procedure specifies different modes of addition of emulsifier whereas the process of our invention specifies procedure of adding emulsifier only to the aqueous phase.

The objective of the invention mentioned in European Patent EP 0700678 (1996) is essentially to overcome the problem of discolouration of lipid emulsion using citric acid and amino acids whereas the objective of the present invention is to develop a oil coated Amphotericin B structured in oil-in-water type emulsion having low toxicity characterised by $LD_{50}$ of at least 400 mg/kg in mice.

Although the present invention has been described with respect to particular embodiments, it will be apparent to those skilled in the art that various changes and modifications can be made without departing from the invention.

EXAMPLES

The invention will now be illustrated by way of examples. The examples are by way of illustration only and in no way restrict the scope of the invention.

All the raw materials used in this example were of parenteral grade. Equipments used were of conventional nature. Entire processing was done in an area with a controlled environment. Nitrogen cover was provided while processing the batch.

Amphotericin B used in these Examples was of parenteral grade obtained from Alpharma complying with USP specifications.

Purified Egg phosphatide used in the Examples was of parenteral grade and was procured from Lipoids.

Commercially available Amphotericin B Injection containing sodium deoxycholate is referred as Conventional Amphotericin B Injection throughout in pharmacokinetic studies, organ distribution studies and toxicity studies. Only one brand of conventional composition is used throughout all the studies.

Example I

Oily phase was prepared by dispersing 1 g of Amphotericin B in 40 g of soybean oil.

Aqueous phase was prepared by adding 4.5 g of Glycerin to 150 ml of water and then dispersing in it 2.4 g of Egg phosphatide. pH was adjusted to 10.6 using aqueous sodium hydroxide solution.

Oily phase prepared above was added to the aqueous phase under high speed stirring. The volume was made upto 200 ml with water. The emulsion formed was passed through the high pressure homogeniser. Homogenisation was repeated till the globule/particle size was below 2 μm. The product was cooled to about 20° C. immediately after each homogenisation cycle.

The homogenised emulsion was filtered through 2μ filter and filled into containers under nitrogen, sealed and sterilised by autoclaving.

The product made by this process has the following composition:

| | |
|---|---|
| a) Amphotericin B | 1.0 g |
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

The sterilised product obtained was subjected to toxicity studies in mice, rats and dogs (Example VIII-A, VIII-B, VIII-C, VIII-D), pharmacokinetic studies (Example IX), organ distribution studies (Example X-A, X-B). Stability studies were carried out by storage of the product in the vials at 2° C.–8° C. and the results are given below.

STABILITY DATA OF PRODUCT OF EXAMPLE I

| PERIOD | APPEARANCE | AMPHOTERICIN B CONTENT |
|---|---|---|
| Initial | Yellow coloured uniform emulsion | 104.6% |
| 6 Months | Yellow coloured uniform emulsion | 101.3% |
| 1 year | Yellow coloured uniform emulsion | 99.4% |

The toxicity studies clearly show that the emulsion prepared by the process of invention is a synergistic composition.

Example II

Amphotericin B powder was micronised using Air jet mill to a particle size range of less than 10 microns.

Oily phase was prepared by dispersing 1 g of Amphotericin B (Micronised) in 40 g of soybean oil.

Aqueous phase was prepared by adding 4.5 g of Glycerin to 150 ml of water and then dispersing in it 2.4 g of Egg phosphatide. pH was adjusted to 10.8 using aqueous sodium hydroxide solution.

Oily phase prepared above was added to the aqueous phase under high speed stirring. The volume was made upto 200 ml with water. The emulsion formed was passed through the high pressure homogeniser. Homogenisation was repeated till the globule/particle size was below 2 μm.

The homogenised emulsion was filtered through 2μ filter and filled into containers under nitrogen, sealed and autoclaved.

The product made by this process has the following composition:

| | |
|---|---|
| a) Amphotericin B (Micronised) | 1.0 g |
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

This Example proves that cooling during homogenisation is not required if micronised Amphotericin B is used.

Example III

Oily phase was prepared by dispersing 1 g of Amphotericin B in 40 g of Soybean oil previously heated to 70° C.

Aqueous phase was prepared by adding 4.5 g of glycerin to 150 ml of water previously heated to 65° C. and then dispersing in it 2.4 g of Egg phosphatide. pH was adjusted to 10.8 using aqueous sodium hydroxide solution.

Oily phase at 70° C. was added to the aqueous phase at 65° C. under high speed stirring. The volume was made upto 200 ml with water. The emulsion formed was passed through the high pressure homogeniser. Homogenisation was repeated till the globule/particle size was below 2 µm. The product was cooled to about 20° C. immediately after each homogenisation cycle.

The homogenised emulsion was filtered through 2µ filter and filled into containers under nitrogen, sealed and sterilised by autoclaving 110° C. for 40 minutes.

The product made by this process has the following composition:

| a) Amphotericin B | 1.0 g |
|---|---|
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

The content of Amphotericin B in the product obtained was analysed and found to be satisfactory indicating that emulsification could be carried out at higher temperature.

Example IV

Oily phase—40 g of Soybean oil

Aqueous phase was prepared by adding 4.5 g of Glycerin to 150 ml of Water and then dispersing in it 2.4 g of Egg phosphatide. 1 g of Amphotericin B was dispersed in this egg phosphatide solution and pH was adjusted to 10.8 using aqueous sodium hydroxide solution.

Oily phase was added to the aqueous phase under high speed stirring. The volume was made upto 200 ml with water. The emulsion formed was passed through the high pressure homogeniser. Homogenisation was repeated till the globule/particle size was below 2 µm. The product was cooled to about 20° C. immediately after each homogenisation cycle.

The homogenised emulsion was filtered through 2µ filter and filled into containers under nitrogen, sealed and sterilised by autoclaving.

The product made by this process has the following composition:

| a) Amphotericin B | 1.0 g |
|---|---|
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

The sterilised product was subjected to toxicity studies as per the details given in Example XI and found to produce toxic symptoms of cardiac toxicity. Hence addition of Amphotericin B to aqueous phase is not recommended.

Example V

Oily phase was prepared by dissolving 2.4 g of Purified egg phosphatide under stirring in 40 g of Soybean oil previously heated to 70° C.

Aqueous phase was prepared by adding 4.5 g of glycerin to 150 ml of water previously heated to 65° C. and then dispersing in it 1 g of Amphotericin B. pH was adjusted to 11.0 using aqueous sodium hydroxide solution.

Oily phase at 70° C. was added to the aqueous phase at 65° C. under high speed stirring. The volume was made upto 200 ml with water. The emulsion formed was passed through the high pressure homogeniser. Homogenisation was repeated till the globule/particle size was below 2 µm. The product was cooled to about 20° C. immediately after each homogenisation cycle.

The homogenised emulsion was filtered through 2µ filter and filled into containers under nitrogen, sealed and sterilised by autoclaving.

The product made by this process has the following composition:

| a) Amphotericin B | 1.0 g |
|---|---|
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

The sterilised product was subjected to toxicity studies as per the details given in Example XI and found to produce toxic symptoms of cardiac toxicity. Hence addition of Purified egg phosphatide to oily phase and addition of Amphotericin B to aqueous phase is not recommended.

Example VI 40 g of Soybean oil was heated to 75° C. and 2.4 g of egg lecithin was dissolved in it under stirring. 1 g of Amphotericin B was dispersed under stirring in oily phase to get a uniform dispersion of Amphotericin B in oily phase. Nitrogen was flushed for 15 minutes in oily phase.

150 ml of Water was heated to 65° C. 4.5 g of Glycerin was added to it under stirring pH was adjusted to 10.65 using dilute sodium hydroxide solution. Amphotericin B oily dispersion was added to this aqueous phase under high speed stirring to get a coarse emulsion. The volume was made upto 200 ml with water. This coarse emulsion was then homogenised using APV high pressure homogeniser till the homogenised product was filterable through 2µ glass fibre filter. The product was cooled to about 20° C. immediately after each homogenisation cycle. The filtered product was filled into glass containers under nitrogen, sealed and sterilised by autoclaving.

The product made by this process has the following composition:

| a) Amphotericin B | 1.0 g |
|---|---|
| b) Soybean oil | 40.0 g |
| c) Purified Egg phosphatide | 2.4 g |
| d) Glycerin | 4.5 g |
| e) Sodium hydroxide | q.s. to adjust the pH |
| f) Water | q.s. to 200 ml |

The sterilised product was subjected to toxicity studies as per the details given in Example XI and found to produce toxic symptoms of cardiac toxicity. Hence addition of Purified egg phosphatide to oily phase is not recommended.

Parenteral composition of oil coated Amphotericin B structured in oil-in-water type emulsion in the following Examples is referred as Amphotericin B Emulsion (5 mg/ml).

Example VII

Amphotericin B Emulsion (5 mg/ml) prepared as per the process and formula of Example I was subjected to in-vitro toxicity test against human red blood corpuscles (RBCs) alongwith conventional Amphotericin B formulation containing sodium deoxycholate.

Material and Method

Test System: RBCs from normal human male donors.

Test Material: Amphotericin B Emulsion (5 mg/ml) prepared as per the process and formula of Example I.

Comparative material: Amphotericin B Conventional Injection (5 mg/ml).

Study Design: Blood was collected in heparinized tubes. RBCs were isolated by centrifugation at 450 g for 10 min at 4° C. The plasma and buffy coat were removed and the RBCs were washed 3 times with phosphate buffer saline (PBS, pH 7.4) at 4° C. before being dispersed in PBS. This was then counted on a Sysmex KX-21 cells counter and used on the day of harvesting. For the determination of RBC sensitivity to Amphotericin B, 2 ml of cell suspension ($5 \times 10^8$ cells/ml) in PBS were incubated for 1 h at 37° C. with Amphotericin B emulsion or Conventional Amphotericin B Injection. The RBCs were then centrifuged for 5 min at 1500 g and washed 3 times with PBS. The pellet of RBCs was lysed by 2 ml of water stirred and centrifuged (1500 g for 5 min) in order to remove membranes. Haemoglobin was measured on the cell counter. Release was calculated as the difference between control and treated cells and was expressed as a percentage of the total haemoglobin content.

TABLE 1

DOSES OF AMPHOTERICIN B FORMULATIONS STUDIED FOR IN VITRO TOXICITY AGAINST HUMAN RBCs

| GROUP NO. | GROUP | DOSE (mg/L) |
|---|---|---|
| 1. | Control | — |
| 2. | Conventional formulation (5 mg/ml) | 5, 50, 100, 200 |
| 3. | Amphotericin B emulsion (5 mg/ml) | 5, 50, 100, 200 |

Statistical Analysis:

The data obtained were analysed by comparing the treated groups with the negative control group using Student's t-test.

Results and Discussion

TABLE 2

HAEMOGLOBIN CONTENT IN G/DL FOR THE AMPHOTERICIN B FORMULATIONS

| | PERCENT HAEMOLYSIS | |
|---|---|---|
| DOSE (mg/L) | Conventional Amphotericin B Injection | Emulsion |
| 5 | 77.5 ± 0.0 | 2.04 ± 0.0 |
| 50 | 100.0 ± 0.0 | 4.08 ± 0.0 |
| 100 | 100.0 ± 0.0 | 4.18 ± 0.82 |
| 200 | 100.0 ± 0.0 | 9.49 ± 4.48 |

There is an increasing haemoglobin leakage with increasing concentrations of Amphotericin B in Conventional Amphotericin B Injection and the emulsion (Refer FIG. 1). Conventional Amphotericin B Injection showed an average leakage of 77.55% for 5 mg/L and 100% for 50 mg/L, 100 mg/L, 200 mg/L. Emulsion showed an average of 2.04% for 5 mg/L, 4.08% for 50 mg/L, 4.18% for 100 mg/L and 9.49% for 200 mg/L. Amphotericin B emulsion was significantly less toxic than Conventional Amphotericin B Injection at the doses studied ($P<0.05$).

Conclusion

Thus the in vitro toxicity data clearly indicate that Amphotericin B emulsion prepared in Example I is less toxic than Conventional Amphotericin B Injection when the target cells are human RBCs.

Example VIII

Amphotericin B Emulsion (5 mg/ml) prepared as per the process and formula of Example I was subjected to in vivo toxicity studies in mice alongwith conventional Amphotericin B containing sodium deoxycholate.

The study was performed with the following aims:

To estimate the $LD_{50}$ values for both the above formulations from single dose studies.

To determine effects on toxicity for above 2 formulations from repeat dose studies.

VIII-A) Single Dose Toxicity Study in Mice

Material and Method

Test System: Female Swiss albino mice in the weight range of 20–22 gm were obtained from the animal house of Bharat Serums & Vaccines Ltd (BSVL) and employed for the study. The animals were provided with standard chow and Aquaguard™ water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Study Design: Animals were divided into 2 groups of 8 animals each viz., GROUP 1 and GROUP 2. GROUP 1 received various doses of Conventional Amphotericin B Injection, GROUP 2 received various doses of Amphotericin B emulsion.

TABLE 3

DOSES OF AMPHOTERICIN B FORMULATIONS STUDIED FOR SINGLE DOSE TOXICITY STUDIES IN MICE

| GROUP NO. | GROUP | DOSE (mg/kg body weight) |
|---|---|---|
| 1. | Conventional Amphotericin B Injection (5 mg/ml) | 5, 7.5, 10, 15, 20 |
| 2. | Amphotericin B emulsion (5 mg/ml) | 50, 100, 150, 200, 250, 300, 350, 375 |

All groups received injections by the intravenous route. All animals were observed for any signs of clinical toxicity and for mortality for a period of 72 hours. The percent mortality was calculated for all the doses.

Statistical Analysis: Probit Analysis method was performed to determine $LD_{50}$ values for all the formulations.

Results and Discussion

TABLE 4

PERCENT MORTALITY FOR THE VARIOUS DOSES OF THE 2 FORMULATIONS

| GROUP | DOSE (mg/kg) | PERCENT MORTALITY |
|---|---|---|
| Conventional Amphotericin B Injection | 2.5 | 33.33 |
| | 5 | 50 |
| | 7.5 | 66.67 |
| | 10 | 83.33 |
| | 15 | 100 |
| | 20 | 100 |
| Amphotericin B emulsion | 50 | 0 |
| | 100 | 0 |
| | 150 | 0 |
| | 200 | 0 |
| | 250 | 16.67 |
| | 300 | 16.67 |
| | 350 | 33.33 |
| | 375 | 42.85 |

Above table indicates that the conventional preparation Conventional Amphotericin B Injection is more toxic than Amphotericin B emulsion. The percent mortality for the formulations increased in a dose-dependent fashion. The $LD_{50}$ values for the 2 formulations were determined by the Probit Analysis method. FIG. 2 gives a plot of percent mortality Vs dose for the 2 formulations.

| FORMULATION | ESTIMATED LD50 (mg/kg) |
|---|---|
| Conventional Amphotericin B Injection | 5 |
| Amphotericin B emulsion | 432.62 |

CONCLUSION: The Amphotericin B emulsion prepared in Example I has high LD50 value and is less toxic than the Conventional Amphotericin B Injection.

VIII-B) Repeat Dose Toxicity Study in Mice

Material and Method

Test System: Female Swiss albino mice in the weight range of 20–22 gm were obtained from the animal house of Bharat Serums & Vaccines Ltd (BSVL) and employed for the study. The animals were provided with standard chow and Aquaguard™ water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Study Design: Animals were divided into 3 groups of 6 animals each viz., GROUP 1, GROUP 2 and GROUP 3. GROUP 1 received the blank emulsion vehicle (Control), GROUP 2 received various doses of Conventional Amphotericin B Injection and GROUP 3 received the various doses of Amphotericin B emulsion.

TABLE 5

DOSES OF AMPHOTERICIN B CONVENTIONAL AND AMPHOTERICIN B EMULSION STUDIED FOR REPEAT DOSE TOXICITY STUDIES IN MICE

| GROUP NO. | GROUP | DOSE (mg/kg body weight) |
|---|---|---|
| 1. | Control | Vehicle |
| 2. | Conventional Amphotericin B Injection (5 mg/ml) | 1.5, 2.5 |
| 3. | Amphotericin B emulsion (5 mg/ml) | 10, 20, 40 |

All groups received injections as stated in Table 5 daily by the intravenous route. The control groups received the maximum volume of the vehicle. All animals were observed for any signs of clinical toxicity. Their body weights were recorded every alternate day for 14 days. Also, the animals were observed for mortality for a period of 14 days. The percent mortality was calculated for all the doses.

Statistical Analysis:

The data obtained were analysed for comparing the change in body weights during the study. Such changes were compared between the treated groups.

Results and Discussion

TABLE 6

PERCENT MORTALITY FOR THE VARIOUS DOSES OF THE 2 FORMULATIONS

| GROUP | DOSE (mg/kg) | PERCENT MORTALITY |
|---|---|---|
| Conventional Amphotericin B Injection | 1.5 | 20 |
| | 2.5 | 80 |
| Amphotericin B emulsion | 10 | 0 |
| | 20. | 0 |
| | 40 | 30 |
| Control | Vehicle | 0 |

Above table (also refer FIG. 3) indicates that Conventional Amphotericin B Injection is more toxic than Amphotericin B emulsion. The percent mortality for the formulations increased in a dose-dependent fashion. No mortality was seen for vehicle treated group for 14 days. Amphotericin B emulsion showed lesser toxicity than Conventional Amphotericin B Injection even at higher doses.

TABLE 7

MEAN BODY WEIGHTS AT VARIOUS DOSES FOR REPEAT DOSE TOXICITY STUDY IN MICE

| GROUP | DOSE (mg/kg) | MEAN BODY WEIGHT ± SDEV IN GMS FOR 14 DAYS | | | | | | | |
|---|---|---|---|---|---|---|---|---|---|
| | | D0 | D2 | D4 | D6 | D8 | D9 | D11 | D12 | D14 |
| Conventional Amphotericin B | 1.5 | 19.56 ± 2.74 | 19.01 ± 2.83 | 18.64 ± 3.81 | 21.33 ± 14.38 | 18.92 ± 4.57 | 19.71 ± 4.36 | 19.94 ± 4.15 | 22.88 ± 4.25 | 19.82 ± 5.04 |

TABLE 7-continued

MEAN BODY WEIGHTS AT VARIOUS DOSES FOR REPEAT DOSE TOXICITY STUDY IN MICE

| GROUP | DOSE (mg/kg) | MEAN BODY WEIGHT ± SDEV IN GMS FOR 14 DAYS | | | | | | | |
|---|---|---|---|---|---|---|---|---|---|
| | | D0 | D2 | D4 | D6 | D8 | D9 | D11 | D12 | D14 |
| Injection | 2.5 | 17.54 ± 3.14 | 15.72 ± 2.92 | 16.88 ± 3.43 | 18.85 ± 1.76 | 16.35 ± 1.62 | 16.05 ± 1.06 | 17.3 ± 1.27 | 19.15 ± 1.34 | 17.7 ± 1.83 |
| Amphotericin B emulsion | 10 | 16.3 ± 1.19 | 17 ± 2.01 | 14.46 ± 1.83 | 19.57 ± 3.04 | 17.51 ± 2.61 | 17.96 ± 2.87 | 19.01 ± 2.59 | 21.21 ± 2.45 | 19.76 ± 2.79 |
| | 20 | 16.95 ± 2.33 | 17.42 ± 1.87 | 16.96 ± 1.99 | 20.61 ± 2.53 | 17.54 ± 2.8 | 17.91 ± 3.03 | 18.83 ± 3.06 | 19.29 ± 3.46 | 19.03 ± 3.78 |
| | 40 | 19.87 ± 2.83 | 18.96 ± 3.36 | 16.43 ± 2.19 | 19.95 ± 2.56 | 17.23 ± 2.75 | 17.53 ± 2.83 | 17.93 ± 2.65 | 19.38 ± 3.01 | 17.88 ± 3.00 |
| Control | 0 | 18.74 ± 1.97 | 17 ± 2.11 | 16.42 ± 3.12 | 16.98 ± 2.87 | 20.86 ± 3.96 | 20.08 ± 4.56 | 21.24 ± 4.39 | 22.26 ± 4.90 | 22.74 ± 4.97 |

D: indicates day of observation; SDEV indicates standard deviation.
Bold: Significantly different from control (treated with the vehicle of Amphotericin B emulsion).

Conventional Amphotericin B Injection treated group showed a decrease in body weight of animals at 1.5 mg/kg and 2.5 mg/kg, whereas Amphotericin B emulsion showed a decrease in body weight of animals from 20 mg/kg and 40 mg/kg (Refer FIG. 4). On days 6 and 8 the body weights of mice treated with Amphotericin B emulsion 20 mg/kg and 40 mg/kg were significantly less than those of Amphotericin B emulsion treated mice at 10 mg/kg.

Histopathological examination showed some degenerative changes in parenchymal cells of liver and kidneys, which may be due to general metabolism in mice. The senous myofibrils probably were a result of hypoxia during sacrifice. The changes in general were of reversible type. The effect of Amphotericin B appeared more on liver and kidneys and to some extent in heart, causing very acute lesions. The intensity, in general, was dose dependent. In Conventional Amphotericin B Injection, the lesions were seen at low dose levels.

Conclusion

The Amphotericin B emulsion showed less toxicity than Conventional Amphotericin B Injection.

VIII-C) Single Dose Toxicity Study in Rats

Material and Method

Test System: Wistar albino rats of either sex in the weight range of 140–160 gm were obtained from the animal house of Bharat Serums & Vaccines Ltd (BSVL) and employed for the study. The animals were provided with standard chow and Aquaguard™ water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Study Design: Animals were divided into 2 groups of 6 animals each viz., GROUP 1 and GROUP 2. GROUP 1 received various doses of Conventional Amphotericin B Injection. GROUP 2 received the doses of Amphotericin B emulsion.

TABLE 8

DOSES OF CONVENTIONAL AMPHOTERICIN B INJECTION AND AMPHOTERICIN B EMULSION STUDIED FOR SINGLE DOSE TOXICITY STUDIES IN RATS

| GROUP NO. | GROUP | DOSE (mg/kg body weight) |
|---|---|---|
| 1. | Conventional Amphotericin B Injection (5 mg/ml) | 1.25, 2.5, 5 |
| 2. | Amphotericin B emulsion (5 mg/ml) | 50, 100, 150 |

All groups received injections as stated in Table 8 by the intravenous route. All animals were observed for any signs of clinical toxicity and for mortality for a period of 72 hours. The percent mortality was calculated for all the doses.

Statistical Analysis:

Probit Analysis method was performed to determine $LD_{50}$ values for all the formulations.

Results and Discussion

TABLE 9

PERCENT MORTALITY FOR THE VARIOUS DOSES OF THE 2 FORMULATIONS

| GROUP | DOSE (mg/kg) | PERCENT MORTALITY |
|---|---|---|
| Conventional Amphotericin B Injection | 1.25 | 0 |
| | 2.5 | 33.33 |
| | 5 | 100 |
| Amphotericin B emulsion | 50 | 0 |
| | 100 | 0 |
| | 150 | 16.67 - after 24 h |
| | | 33.33 - after 48 h |
| | | 50 - after 72 h |

Above table (also refer FIG. 5) indicates that Conventional Amphotericin B Injection is more toxic than Amphotericin B emulsion. The percent mortality for the formulations increased in a dose-dependent fashion. The $LD_{50}$ values for the 2 formulations were determined by the Probit Analysis method. The 50% mortality was observed for Amphotericin B emulsion after 72 hours. There was no change in body weights over 72 hours.

| FORMULATION | ESTIMATED LD50 (mg/kg) |
|---|---|
| Conventional Amphotericin B Injection | 2.5–5 |
| Amphotericin B emulsion | >100 |

Conclusion

The Amphotericin B emulsion is less toxic than Conventional Amphotericin B Injection.

VIII-D) Single Dose Toxicity Study in Dogs

The present study was conducted with an aim to evaluate the toxicity and safety of Amphotericin B emulsion in dogs.

Material and Method

Test System: Twelve healthy dogs of either sex weighing on an average 10–15 kg were employed in this study. The animals were housed under standard conditions in Kennel with access to food and water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Study Design: Animals were divided into 2 groups of 6 animals each viz., GROUP 1 and GROUP 2. GROUP 1 received Conventional Amphotericin B Injection. GROUP 2 received Amphotericin B emulsion prepared in Example I.

TABLE 10

DETAILS OF DOSES OF CONVENTIONAL AMPHOTERICIN B INJECTION AND AMPHOTERICIN B EMULSION STUDIED FOR SINGLE DOSE TOXICITY STUDIES IN DOGS

| GROUP NO. | GROUP | DOSE (mg/kg body weight) |
|---|---|---|
| 1. | Conventional Amphotericin B Injection (5 mg/ml) | 1 |
| 2. | Amphotericin B emulsion (5 mg/ml) | 1 |

All groups received injections as stated in Table 10, dissolved in 6–20 ml of 5% dextrose by the intravenous route. All animals were observed for any signs of clinical toxicity and for a period of 21 days after injection. The animals were weighed at visit V0, V2, V4, V6 and V8. Blood was collected for hematological and biochemical studies (kidney function and liver function test) on V0, V4 and V8.

Visit Schedule:

| V0 | Baseline visit | V5 | After 12 days of V0 |
|---|---|---|---|
| V1 | Within 2 days of baseline visit | V6 | After 15 days of V0 |
| V2 | After 3 days of V0 | V7 | After 18 days of V0 |
| V3 | After 6 days of V0 | V8 | After 21 days of V0 |
| V4 | After 9 days of V0 | | |

| Visit | V0 | V1 | V2 | V3 | V4 | V5 | V6 | V7 | V8 |
|---|---|---|---|---|---|---|---|---|---|
| Administration of Drug | | X | X | X | X | X | X | X | X |
| Hematology and Biochemistry | X | | | | X | | | | X |

Statistical Analysis:

The data obtained were analysed for comparing the change in parameters from the baseline during the study. Such changes were compared between the treated groups.

Results and Discussion

TABLE 11

MEAN PERCENT CHANGE OF HEMATOLOGICAL PARAMETERS OVER BASELINE AT VARIOUS VISITS IN DOGS.

PERCENT CHANGE IN HEMATOLOGICAL PARAMETERS ± SD

| GROUP | VISIT | RBC | Hemoglobin | MCV | Hematocrit | WBC (Total) | Neutrophil | Lymphocyte | Monocyte | Eosinophil | Basophil |
|---|---|---|---|---|---|---|---|---|---|---|---|
| Conventional Amphotericin B Injection | V4 | −6.61 ± 2.58 | −9.37 ± 5.26 | −4.29 ± 3.75 | −10.46 ± 4.77 | −14.68 ± 16.77 | −11.37 ± 4.07 | −26.86 ± 10.81 | −9.36 ± 33.46 | 23.33 ± 49.15 | 0.0 ± 0.0 |
| | V8 | −10.24 ± 238 | −21.68 ± 2.15 | −7.31 ± 4.29 | −16.91 ± 4.95 | −13.66 ± 16.93 | −15.07 ± 6.23 | −30.02 ± 13.96 | −23.13 ± 37.5 | 6.11 ± 54.83 | 0.0 ± 0.0 |
| Amphotericin B emulsion | V4 | −8.69 ± 3.4 | −16.28 ± 8.24 | −10.31 ± 13.92 | −18.13 ± 11.51 | −34.91 ± 6.96 | −5.65 ± 3.44 | −22.23 ± 14.68 | 13.39 ± 25.39 | 67.85 ± 68.57 | 0.0 ± 0.0 |
| | V8 | −14.7 ± 5.63 | −10.9 ± 44.77 | −12.57 ± 16.26 | −25.45 ± 13.77 | −32.7 ± 8.52 | −9.21 ± 7.65 | −21.84 ± 18.71 | 0.69 ± 12.95 | 25.19 ± 52.32 | 0.0 ± 0.0 |

SD indicates standard deviation.
Bold: Significant difference between the 2 formulation groups for leukocyte and neutrophil on V4 and V8

All hematological parameters were found to show variation from baseline values in both the groups. The percent fall in leukocyte count for emulsion was significantly higher than conventional but was within the normal range and thus of no clinical significance.

TABLE 12

MEAN PERCENT CHANGE OF BIOCHEMICAL PARAMETERS
IN DOGS OVER BASELINE AT VARIOUS VISITS

PERCENT CHANGE IN BIOCHEMICAL PARAMETERS ± SD

| | | LIVER VALUES | | | KIDNEY VALUES | |
|---|---|---|---|---|---|---|
| | | SGOT | SGPT | Total | | |
| GROUP | VISIT | (AST) | (ALT) | Bilirubin | BUN | CREATININE |
| Conventional Amphotericin B Injection | V4 | 143.22 ± 25.89 | 114.77 ± 35.33 | 140.9 ± 27.92 | 86.45 ± 25.15 | 81.13 ± 32.26 |
| | V8 | 334.38 ± 40.87 | 261.37 ± 57.27 | 259.11 ± 73.74 | 309.35 ± 38.57 | 214.62 ± 56.49 |
| Amphotericin B emulsion | V4 | 77.11 ± 33.72 | 39.30 ± 18.49 | 87.88 ± 25.25 | 8.08 ± 48.00 | 25.93 ± 11.16 |
| | V8 | 108.86 ± 38.91 | 60.79 ± 26.55 | 153.55 ± 28.65 | 51.59 ± 4.86 | 165.28 ± 86.21 |

SD indicates standard deviation.
Bold: Significant difference between the 2 formulation groups on V4 and V8

The liver function parameter (Refer FIG. 6), AST showed 334.38% rise by V8 in Conventional Amphotericin B Injection group, whereas it was limited only to 108.86% in Amphotericin B emulsion group. Similar findings were seen for ALT and total bilirubin. The rise for conventional group was statistically significant as compared to emulsion.

The kidney function parameters (Refer FIG. 7) were significantly deranged in the Conventional Amphotericin B Injection group. The deviation in Amphotericin B emulsion was significantly less than that of Conventional Amphotericin B Injection group.

Nephrotoxicity, the primary toxicity of Amphotericin B results from the non-selective cytotoxic interaction between Amphotericin B of Conventional Amphotericin B Injection (containing sodium deoxycholate) and cholesterol of mammalian cells. Mammalian cytotoxicity is attenuated by incorporating Amphotericin B in lipid based emulsion formulation. This alters the affinity of Amphotericin B and decreases its selective transfer to cholesterol containing mammalian cells.

TABLE 13

MEAN BODY WEIGHTS AT VARIOUS DOSES FOR SINGLE
DOSE TOXICITY STUDY IN DOGS

| | | MEAN BODY WEIGHT ± SD IN GMS FOR 14 DAYS | | | | |
|---|---|---|---|---|---|---|
| GROUP | DOSE (mg/kg) | V0 | V2 | V4 | V6 | V8 |
| Conventional Amphotericin B Injection | 1 | 15.0 ± 3.85 | 14.33 ± 3.38 | 14.0 ± 3.17 | 13.66 ± 3.12 | 13.166 ± 3.12 |
| Amphotericin B emulsion (BSVL) | 1 | 15.5 ± 2.96 | 15.0 ± 3.01 | 15.0 ± 2.774 | 14.5 ± 2.68 | 14.16 ± 2.639 |

SD indicates standard deviation.

Conventional Amphotericin B Injection treated group showed a greater decrease in body weights of animals as compared to Amphotericin B emulsion (Refer FIG. 8).

Conclusion

Amphotericin B emulsion offers significant protection against hepatotoxicity and nephrotoxicity as compared to Conventional Amphotericin B Injection.

Example IX

Amphotericin B Emulsion (5 mg/ml) prepared as per the process and formula of Example I was used to evaluate the pharmacokinetic parameters in rabbits in comparison with the Conventional Amphotericin B Injection.

Material and Method

Test System: Male New Zealand white rabbits in the weight range of 1.5–2.0 kg were obtained from the animal house of Bharat Serums & Vaccines Ltd (BSVL) and employed for the study. The animals were provided with standard nutritional vegetables and Aquaguard™ water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Study Design: Animals were divided into 2 groups of 3 animals each viz., GROUP 1 and GROUP 2. GROUPS 1, and 2 received Conventional Amphotericin B Injection and Amphotericin B emulsion respectively. Blood samples were collected at 5, 15, 30, 45, and 60 mins and after 1, 2, 3, 4, 5, 24, and 48 hours after single intravenous bolus dose. The samples were centrifuged at 3000–4000 rpm to separate plasma. The plasma was stored at −20° C. until analysis.

Route of administration: Via the marginal ear vein of rabbits.

TABLE 14

DOSES OF AMPHOTERICIN B FORMULATIONS FOR
PHARMACOKINETIC STUDIES IN RABBITS

| GROUP NO. | GROUP | DOSE (mg/kg body weight) |
|---|---|---|
| 1. | Conventional Amphotericin B Injection (5 mg/ml) | 1 |
| 2. | Amphotericin B emulsion (5 mg/ml) | 5 |

Analysis of Amphotericin B Content

Amphotericin B content in plasma was analyzed by phase HPLC method using C-18 column. Amphotericin B in plasma was extracted using HPLC grade dimethyl sulfoxide and acetonitrile in a ratio of 1:3:1. The samples were then centrifuged at 3000 rpm and the supernatant was injected into the column.

Statistical Analysis:

The data obtained were analysed for comparing the treated groups by Student's t-test.

Results and Discussion

TABLE 15

GIVES THE PHARMACOKINETIC PARAMETERS FOR THE 2 FORMULATIONS.

| | Plasma concentration (mcg/ml) | |
| --- | --- | --- |
| Time (hrs) | Amphotericin B Emulsion (5 mg/kg) | Conventional Amphotericin B Injection (1 mg/kg) |
| 0.083 | 0.387 ± 0.176 | 0.499 ± 0.133 |
| 0.25 | 0.196 ± 0.101 | 0.274 ± 0.076 |
| 0.5 | 0.119 ± 0.018 | 0.313 ± 0.118 |
| 0.75 | 0.103 ± 0.0065 | 0.463 ± 0.0 |
| 1 | 0.099 ± 0.0078 | 0.245 ± 0.007 |
| 2 | 0.099 ± 0.0 | 0.216 ± 0.0035 |
| 3 | 0.094 ± 0.0 | 0.365 ± 0.159 |
| 4 | 0.093 ± 0.0 | 0.24 ± 0.081 |
| 5 | 0.092 ± 0.0 | 0.175 ± 0.012 |
| 24 | 0.0 ± 0.0 | 0.173 ± 0.155 |
| 48 | 0.0 ± 0.0 | 0.066 ± 0.0 |

| PARAMETERS | Conventional Amphotericin B Injection (1 mg/kg) | Amphotericin B Emulsion (5 mg/kg) |
| --- | --- | --- |
| $C_{max}$ (mcg/ml) | 0.576 ± 0.006 | 0.387 ± 0.176 |
| $T_{max}$ (hours) | 0.083 ± 0.0 | 0.083 ± 0.0 |
| $T_{1/2}$ (hours) | 1.89 ± 0.728 | 6.622 ± 10.63 |
| AUC (mcg-hr/ml) | 1.851 ± 0.836 | 1.115 ± 1.558 |
| Vd (L) | 1.47 ± 1.26 | 26.144 ± 18.522 |
| Cl (ml/hr) | 540.25 ± 28.01 | 16062.31 ± 12510.82 |

There is no significant difference in $C_{max}$, $T_{max}$, $T_{1/2}$, Vd between the two formulations. With regards to clearance, emulsion is removed from the plasma at a significantly faster rate than Conventional Amphotericin B Injection (P<0.05). This indicates that the distribution of the emulsion into the tissues occurs more rapidly than Conventional Amphotericin B Injection (Refer FIG. 9).

Example X

Amphotericin B Emulsion (5 mg/ml) prepared as per the process and formula of Example I was used for organ distribution studies in mice in comparison with the Conventional Amphotericin B Injection.

The present study was performed with the following aims:
To estimate the pattern of organ distribution in mice for the 2 formulations from single dose studies.
To determine the pattern of organ distribution in mice for the 2 formulations from repeat dose studies.

X-A) Single Dose Organ Distribution Study in Mice

Material and Method

Test System: Female Swiss albino mice in the weight range of 20–22 gm were obtained from the animal house of Bharat Serums & Vaccines Ltd (BSVL) and employed for the study. The animals were provided with standard chow and Aquaguard™ water, ad libitum.

Test Material: Amphotericin B Emulsion (5 mg/ml) prepared as per the process and formula of Example I was administered intravenously as a bolus dose.

Comparative material: Conventional Amphotericin B Injection (5 mg/ml) was administered intravenously as a bolus dose.

Route of administration: Intravenous

Study Design: Animals were divided into 2 groups of 20 animals each viz., GROUP 1 and GROUP 2. GROUP 1 received Conventional Amphotericin B Injection in a dose of 1 mg/kg and GROUP 2 received Amphotericin B emulsion in a dose of 5 mg/kg. Each sampling point consisted of 4 mice. Organ samples namely, liver, lungs, kidneys, spleen and the brain were dissected out at the end of the respective time points, i.e., 0.5, 1, 2, 4, 24 hrs. The organs were immediately frozen to arrest any enzymatic reactions. The organs were weighed and 3 times the volume of water was added. This was then homogenized.

TABLE 16

DOSES OF CONVENTIONAL AMPHOTERICIN B INJECTION AND AMPHOTERICIN B EMULSION STUDIED FOR SINGLE DOSE ORGAN DISTRIBUTION STUDIES IN MICE

| GROUP NO. | GROUP | DOSE (mg/kg body weight) |
| --- | --- | --- |
| 1. | Conventional Amphotericin B Injection (5 mg/ml) | 1 |
| 2. | Amphotericin B emulsion (5 mg/ml) | 5 |

Analysis of Amphotericin B Content

Methanol was added to the homogenate in a ratio of 3:1. This was then centrifuged at a high speed of 13,000–14,000 rpm. The supernatant was then injected into the HPLC column for Amphotericin B analysis.

Statistical Analysis:

The data obtained were analysed for comparing the treated groups by Student's t-test.

Results and Discussion

TABLE 17

GIVES THE ORGAN DISTRIBUTION PARAMETERS FOR THE 2 FORMULATIONS

| ORGAN | PARAMETER | Conventional Amphotericin B Injection (1 mg/kg) | Emulsion (5 mg/kg) |
| --- | --- | --- | --- |
| LIVER | $C_{max}$ (mcg/g) | 3.53 | 26.95 |
| | $T_{max}$ (hours) | 1.0 | 24 |
| | $T_{1/2}$ (hours) | 14.5 | 34.61 |
| | AUC (mcg-hr/ml) | 79.97 | 1227.68 |
| | Cl (ml/br) | 12.51 | 4.07 |
| SPLEEN | $C_{max}$ (mcg/g) | 2.02 | 29.3 |
| | $T_{max}$ (hours) | 0.5 | 24 |
| | $T_{1/2}$ (hours) | 48.98 | −113.88* |
| | AUC (mcg-hr/ml) | 88.58 | 1836 |
| | Cl (ml/br) | 11.29 | −2.72* |
| LUNGS | $C_{max}$ (mcg/g) | 1.29 | 1.64 |
| | $T_{max}$ (hours) | 2.0 | 4 |
| | $T_{1/2}$ (hours) | 48.87 | 212.63 |
| | AUC (mcg-hr/ml) | 89.69 | 510.93 |
| | Cl (ml/hr) | 11.15 | 9.786 |
| KIDNEY | $C_{max}$ (mcg/g) | 1.15 | 0.437 |
| | $T_{max}$ (hours) | 0.5 | 4 |
| | $T_{1/2}$ (hours) | 59.27 | 6.69 |
| | AUC (mcg-hr/ml) | 75.45 | 0.632 |
| | Cl (ml/hr) | 13.26 | 7911.39 |

*sign indicates build-up of Amphotericin B in tissue.

As compared to Conventional Amphotericin B Injection, Amphotericin B emulsion shows high levels in all organs except for the kidney (Refer FIGS. 10a to 10d). Higher half-life values and lower clearance rates of emulsion further support this data. Thus the uptake of Amphotericin B from emulsion into the organs was found to be higher than for Conventional Amphotericin B Injection, being statistically significant in the case of spleen (P<0.05).

Nephrotoxicity is the major drawback associated with Amphotericin B therapy and is due to high levels of Amphotericin B in the kidney. From the $AUC_{(0-\infty)}$ it is clearly evident that emulsion achieves significantly low levels of Amphotericin B than Conventional Amphotericin B Injection (P<0.05). Also emulsion was cleared faster from the kidneys, which accounts for low toxicity and higher $LD_{50}$ value as compared to the Conventional Amphotericin B Injection formulation.

Despite decreasing plasma concentrations, the levels in liver and spleen continued to increase. Similar observations have been reported for liposomes which proposes that liposomal drugs in reticuloendothelial tissues are not in free equilibrium with plasma as are non-liposomal drugs. (Feilding, R M., et al, 1998). This possibly explains the high retention of Amphotericin B in reticuloendothelial tissues in case of emulsion as compared to Conventional Amphotericin B Injection.

X-B) Repeat Dose Organ Distribution Study in Mice

Material and Method

Test System: Female Swiss albino mice in the weight range of 20–22 gm were obtained from the animal house of Bharat Serums & Vaccines Ltd (BSVL) and employed for the study. The animals were provided with standard chow and Aquaguard™ water, ad libitum.

Test Material: Amphotericin B Emulsion (5 mg/ml) prepared as per the process and formula of Example I was administered intravenously as a bolus dose Comparative material: Conventional Amphotericin B Injection (5 mg/ml) was administered intravenously as a bolus dose.

Study Design:

The animals were divided into 2 groups of 24 each. GROUP 1 and GROUP 2. GROUP 1 received Conventional Amphotericin B Injection in a dose of 1 mg/kg and GROUP 2 received Amphotericin B emulsion in a dose of 5 mg/kg. 12 animals were dosed for a period of 7 and the other 12 were dosed for 14 days. Liver, lung, kidney and spleen were dissected out after 6 hrs of the last dose. The organs were immediately frozen to arrest any enzymatic reactions. The organs were weighed and water equivalent to 3 times the organ weight was added. This was then homogenized.

Route of Administration: Intravenous

TABLE 18

DOSES OF CONVENTIONAL AMPHOTERICIN B INJECTION AND AMPHOTERICIN B EMULSION STUDIED FOR SINGLE DOSE ORGAN DISTRIBUTION STUDIES IN MICE

| GROUP NO. | GROUP | DOSE (mg/kg body weight) |
| --- | --- | --- |
| 1. | Conventional Amphotericin B Injection (5 mg/ml) | 1 |
| 2. | Amphotericin B emulsion (5 mg/ml) | 5 |

Analysis of Amphotericin B Content

Amphotericin B content in plasma was analyzed by HPLC method using C-18 column. Amphotericin B in plasma was extracted using HPLC grade methanol in a ratio of plasma to methanol 1:3. The samples were then centrifuged at 3000 rpm and the supernatant was injected into the column.

Statistical Analysis:

The data obtained were analysed for comparing the treated groups by Student's t-test.

Results and Discussion

TABLE 19

GIVES THE ORGAN DISTRIBUTION PARAMETERS FOR THE 2 FORMULATIONS

| | ORGAN CONCENTRATION (mcg/g) | | | |
| --- | --- | --- | --- | --- |
| | Conventional Amphotericin B Injection (1 mg/kg) | | Emulsion (5 mg/kg) | |
| ORGAN | 7 day | 14 day | 7 day | 14 day |
| LIVER | 15.22 ± 4.34 | 15.33 ± 3.45 | 65.34 ± 16.14 | 63.45 ± 9.86 |
| SPLEEN | 4.79 ± 1.04 | 5.05 ± 0.51 | 109.08 ± 15.5 | 75.4 ± 11.32 |
| KIDNEY | 2.21 ± 0.27 | 2.53 ± 0.39 | 2.71 ± 0.5 | 1.97 ± 0.65 |
| LUNGS | 3.66 ± 0.75 | 3.03 ± 0.65 | 18.12 ± 6.96 | 11.32 ± 3.08 |

It was interesting to observe that the tissue concentrations did not substantially increase from the $7^{th}$ to $14^{th}$ dose (Refer FIGS. 11a and 11b) which is in agreement with literature (Olsen, S J, et al, 1991). There were no deaths in the Amphotericin B emulsion treated group despite the elevated Amphotericin B tissue levels. In contrast to this, Conventional Amphotericin B Injection did show mortality during the study period.

It can be seen that the Amphotericin B levels in the kidneys are the same for Conventional Amphotericin B Injection and the emulsion in spite of vast difference observed in nephrotoxicity. A possible reason for this could be that it is the Amphotericin B that is being estimated in the organs regardless of whether it is present as a complex with the lipids or as free drug. In case of Conventional Amphotericin B Injection, Amphotericin B is predominantly present in the free form and hence is nephrotoxic. But in case of the lipid-based emulsion, Amphotericin B possibly exists as a complex with the lipids, which does not exert its toxicity on the tissues.

Amphotericin B, being an amphiphilic drug, exists as soluble monomer or as self-associated oligomers and above the critical micelle concentration it forms micelles. Any factors modifying the equilibrium between the different species of Amphotericin B in aqueous media may change its overall activity and toxicity. Tabosa Do Egito, (1996) consider the Amphotericin B emulsion to act as a reservoir of the monomeric form of Amphotericin B. This highly stable formulation steadily releases only limited amounts of free Amphotericin B monomer. This form may probably bind only to the ergosterol of the fungal cells and posses reduced interaction with the cholesterol of mammalian cells (Tabosa Egito, et al, 1996). Hence the emulsion although shows similar levels as Conventional Amphotericin B Injection is not severely toxic.

Conclusion

Amphotericin B emulsion was formulated with an aim to:
1. Improve the safety profile
2. Make it cost effective The toxicity studies show that the safety margin of the emulsion is indeed an improvement over, Conventional Amphotericin B Injection. This can be attributed to the form in which the emulsion presents itself to its target fungal cells. Conventional Amphotericin B Injection releases Amphotericin B in very large quantities and the monomers thus released associate to form oligomers which, bind to the mammalian cells as well, leading to severe toxicity. On the contrary, the emulsion is not able to achieve such high concentrations in plasma due to rapid phagocytosis by the RES and shows slow progressive release of monomers. This explains the selective action of the emulsion on the fungal cells and hence the low toxicity (Tabosa Do Egito, E S, et al, 1996). The low plasma levels and rapid distribution of Amphotericin B emulsion into the organs is also an advantage over the Conventional Amphotericin B Injection with regards to its targeting potential. Moreover, Amphotericin B emulsion is a cost-effective product in comparison to other lipid based formulations like the lipid complex & liposome preparations.

Thus, Amphotericin B emulsion of the present invention is a promising candidate for targeting therapy of fungal infections.

Example XI

Amphotericin B emulsion prepared in Example IV, Example V and Example VI were subjected to in-vivo toxicity studies in mice.

Single Dose Toxicity Study in Mice

Material and Method

Test System: Female Swiss albino mice in the weight range of 20–22 gm were obtained from the animal house of Bharat Serums & Vaccines Ltd (BSVL) and employed for the study. The animals were provided with standard chow and Aquaguard™ water, ad libitum.

Test Material: Amphotericin B emulsion (5 mg/ml) prepared in Example IV, Example V and Example VI were administered intravenously as a bolus dose.

Comparative material: Amphotericin B Emulsion (5 mg/ml) prepared as per the process and formula of Example I was administered intravenously as a bolus dose.

All groups received injections by the intravenous route. All animals were observed for any signs of clinical toxicity and for mortality for a period of 72 hours. The percent mortality was calculated for all the doses.

Observations:

The groups which received samples from Example IV, Example V & Example VI produced symptoms of cardiac toxicity such as severe respiratory distress, local irritation, abdominal distress and agitation. However these toxic symptoms were not observed in the group which received samples prepared by the process and formula of Example I.

The Advantages of the Invention:

Formulating Amphotericin B as structured emulsion of oil-in-water type for parenteral administration by process of the present invention reduced its toxicity considerably and ensured sterility without altering its antifungal activity.

Amphotericin B incorporated in the oily phase of the emulsion prepared by the process of the present invention remains stable throughout the entire process of manufacturing including autoclaving process of sterilisation and thereafter till its shelf life or use.

Average oil droplet size in the parenteral composition of oil coated Amphotericin B structured in oil-in-water type emulsion prepared by the process of present invention is controlled in the optimum range so that it is preferably distributed in reticulo-endothelial system giving a low plasma concentration.

The invention claimed is:

1. A parenteral composition of oil-coated-Amphotericin B in structured-emulsion form, having $LD_{50}$ of at least 400 mg/kg in mice, comprising
    a) oily phase (up to 30% w/v of the composition) consisting essentially of one or more vegetable oil excluding medium chain triglyceride oils;
    b) a solid powder of Amphotericin B (0.05% to 1% w/v of the composition) dispersed in the oily phase;
    c) aqueous phase water;
    d) tonicity modifying agent selected from the group consisting of glycerin, mannitol, and dextrose dissolved in the aqueous phase; and
    e) natural phosphatide emulsifier (up to 3% w/v of the composition) dispersed in the aqueous phase.

2. A parenteral composition of oil-coated-Amphotericin B in structured-emulsion form as claimed in claim 1 wherein, the oily phase is from about 10% to 20% w/v of the composition.

3. A parenteral composition of oil-coated-Amphotericin B in structured-emulsion form as claimed in claim 1 wherein, the vegetable oil used is soybean oil.

4. A parenteral composition of oil-coated-Amphotericin B in structured-emulsion form as claimed in claim 3 wherein, the content of soybean oil is about 20% w/v of the composition.

5. A parenteral composition of oil-coated-Amphotericin B in structured-emulsion form as claimed in claim 1 wherein, the content of Amphotericin B is about 0.5% w/v of the composition.

6. A parenteral composition of oil-coated-Amphotericin B in structured-emulsion form as claimed in claim 1 wherein, the natural phosphatide used is purified egg phosphatide.

7. A parenteral composition of oil-coated-Amphotericin B in structured-emulsion form as claimed in claim 6 wherein, the content of purified egg phosphatide is about 1.2% w/v of the composition.

8. A parenteral composition of oil-coated-Amphotericin B in structured-emulsion form as claimed in claim 1 wherein, tonicity modifier used is glycerin.

9. A parenteral composition of oil-coated-Amphotericin B in structured-emulsion form as claimed in claim 8 wherein, content of glycerin is about 2.25% w/v of the composition.

10. A parenteral composition of oil-coated-Amphotericin B in structured-emulsion form as claimed in claim 1 wherein, the emulsion comprises a solid powder of Amphotericin B (0.5% w/v of the composition); oily phase is soybean oil (20% w/v of the composition); emulsifier is purified egg phosphatide (1.2% w/v of the composition); tonicity modifying agent is glycerin (2.25% w/v of the composition) and; water (q.s. to 100% by volume of the composition).

11. A process for manufacture of a parenteral composition of oil-coated-Amphotericin B in structured-emulsion form, having LD50 of at least 400 mg/kg in mice as claimed in claim 1 comprising
    i) dispersing the solid powder of Amphotericin B in the oily phase ii) dissolving the tonicity modifying agent in the aqueous phase water;
iii) dispersing the emulsifying agent in the aqueous phase;
iv) adjusting the pH of the aqueous phase to about 8–11;
v) adding the oily phase to the aqueous phase under stirring to obtain a coarse structured-emulsion;
vi) homogenizing the coarse structured-emulsion to a particle size below 2 microns;
vii) filtering and filling the homogenized structured-emulsion into glass containers under nitrogen;
viii) closing the glass containers;
ix) sealing the closed glass containers; and
x) sterilizing the sealed filled containers by autoclaving.

12. A process for manufacture of a parenteral composition of oil-coated-Amphotericin B in structured-emulsion form as claimed in claim 11 wherein, the oily phase or the aqueous phase or both the phases are maintained at a temperature of up to 75° C. during the emulsification process.

13. A process for manufacture of a parenteral composition of oil-coated-Amphotericin B in structured-emulsion form as claimed in claim 11 wherein, sodium hydroxide solution in water is added to adjust the pH between 8 and 11 of the aqueous phase containing emulsifier egg phosphatide.

14. A process for manufacture of a parenteral composition of oil-coated-Amphotericin B in structured-emulsion form as claimed in claim 11 comprising dispersing the solid powder of Amphotericin B in soybean oil; preparing aqueous phase by adding glycerin to water; followed by dispersing the purified egg phosphatide in the aqueous phase, adjusting pH of the aqueous phase to 10.8; adding the soybean oil containing solid powder of Amphotericin B dispersed in it to the aqueous phase containing egg phosphatide dispersed in it under stirring to obtain a coarse structured-emulsion; homogenizing the coarse structured-emulsion to a particle size below 2 microns; filtering through 2 micron filter, filling the homogenized structured-emulsion into glass containers under nitrogen, closing the glass containers, sealing the closed glass containers and sterilizing the sealed filled containers by autoclaving.

* * * * *